US005770211A

United States Patent [19]

Wasmoen et al.

[11] Patent Number: 5,770,211

[45] Date of Patent: Jun. 23, 1998

[54] RECOMBINANT RACCOON POX VIRUSES AND THEIR USE AS AN EFFECTIVE VACCINE AGAINST FELINE INFECTIOUS PERITONITIS VIRUS DISEASE

[75] Inventors: Terri Wasmoen; Lloyd Chavez; Hsien-Jue Chu, all of Fort Dodge, Iowa

[73] Assignee: American Home Products Corporation, Madison, N.J.

[21] Appl. No.: 480,210

[22] Filed: Jun. 7, 1995

Related U.S. Application Data

[62] Division of Ser. No. 125,516, Sep. 22, 1993, abandoned.

[51] Int. Cl.[6] ...................... A61K 39/215; A61K 39/275; A61K 39/295; C12N 7/01

[52] U.S. Cl. .................................... 424/199.1; 435/235.1; 435/320.1; 424/201.1; 424/202.1; 424/221.1

[58] Field of Search ............................. 435/235.1, 320.1; 424/199.1, 221.1, 232.1, 201.1, 202.1

[56] References Cited

U.S. PATENT DOCUMENTS

| | | | |
|---|---|---|---|
| 4,293,653 | 10/1981 | Horzinek et al. | 435/237 |
| 4,303,644 | 12/1981 | Davis | 424/89 |
| 4,571,386 | 2/1986 | Fishman et al. | 435/235 |
| 5,242,686 | 9/1993 | Chu et al. | 424/263.1 |
| 5,266,313 | 11/1993 | Esposito et al. . | |

FOREIGN PATENT DOCUMENTS

| | | | |
|---|---|---|---|
| 0 264 979 A1 | 9/1987 | European Pat. Off. | 15/50 |
| 0 411 684 A2 | 7/1990 | European Pat. Off. | 15/50 |
| 0 376 744 | of 1990 | WIPO . | |
| WO 92/08487 | 5/1992 | WIPO . | |
| WO 9301284 | 1/1993 | WIPO . | |

OTHER PUBLICATIONS

Olsen, *Veterinary Microbiology*, 36:1–37, 1993.
Gerber et al., *Vaccine*, 8:536–542, 1990.
Scott et al., *Feline Health Topics*, 7:6–8, 1992.
De Groot et al., *J. gen. Virol.*, 68:995–1002, 1987.
De Groot et al., *J. gen. Virol.*, 68:2639–2646, 1987.
De Groot et al., *Virology*, 167:370–376, 1988.
Esposito et al., *Vaccines*, 89:403–408, 1989.
Esposito et al., *Vaccines*, 92:321–328, 1992.
Esposito et al., *Virology*, 165:313–316, 1988.
Artois et al., *Can J Vet Res* 54:504–507, 1990.
Binns et al., *Recombinant Poxvirus, CRC Press*, 5:163–205, 1992.
Lodmell et al., *Journal of Virology*, 65:3400–3405, 1991.
Vennema et al., *Virology*, 181:327–335, 1991.
Pedersen et al., *Am J Vet Res*, 44:229–234, 1983.
Stoddart et al., *Res Vet Sci*, 45:383–388, 1988.
Vennema et al., *J. Virol.*, 64:1407–1409, 1990.
Barlough et al., *Canadian J Comp Med*, 49:303–307, 1985.
Barlough et al., *Laboratory Animal Science*, 34:592–597, 1984.
Pedersen, N.C., *Advances in Veterinary Science and Comparative Medicine*, 33:413–428, 1989.

*Primary Examiner*—Mary E. Mosher
*Attorney, Agent, or Firm*—Darby & Darby

[57] ABSTRACT

This invention provides a recombinant raccoon poxvirus that expresses the nucleocapsid and transmembrane proteins of Feline Infectious Peritonitis Virus. The recombinant viruses are useful as vaccines, either alone or in combination with carriers and adjuvants.

13 Claims, 29 Drawing Sheets

FIG. 1A

```
             10          20          30          40
              *           *           *           *
ATG AAG TAC ATT TTG CTA ATA CTC GCG TGC ATA ATT GCA TGC GTT TAT
TAC TTC ATG TAA AAC GAT TAT GAG CGC ACG TAT TAA CGT ACG CAA ATA
 M   K   Y   I   L   L   I   L   A   C   I   I   A   C   V   Y>
   a   a   a   a    TRANSLATION OF FIPV E1 a   a   a   a   a   >

50          60          70          80          90
 *           *           *           *           *
GGT GAA CGC TAC TGT GCC ATG CAA GAC AGT GGC TTG CAG TGT ATT AAT
CCA CTT GCG ATG ACA CGG TAC GTT CTG TCA CCG AAC GTC ACA TAA TTA
 G   E   R   Y   C   A   M   Q   D   S   G   L   Q   C   I   N>
   a   a   a   a    TRANSLATION OF FIPV E1 a   a   a   a   a   >

   100         110         120         130         140
     *           *           *           *           *
GGC ACA AAT TCA AGA TGT CAA ACC TGC TTT GAA CGT GGT GAT CTT ATT
CCG TGT TTA AGT TCT ACA GTT TGG ACG AAA CTT GCA CCA CTA GAA TAA
 G   T   N   S   R   C   Q   T   C   F   E   R   G   D   L   I>
   a   a   a   a    TRANSLATION OF FIPV E1 a   a   a   a   a   >

    150         160         170         180         190
      *           *           *           *           *
TGG CAT CTT GCT AAC TGG AAC TTC AGC TGG TCT GTA ATA TTG ATT GTT
ACC GTA GAA CGA TTG ACC TTG AAG TCG ACC AGA CAT TAT AAC TAA CAA
 W   H   L   A   N   W   N   F   S   W   S   V   I   L   I   V>
   a   a   a   a    TRANSLATION OF FIPV E1 a   a   a   a   a   >
A ----------------------------------------------------------------- A
```

FIG. 1B

```
A---------------------------------------------------------------------A
         200        210        220        230        240
           *          *          *          *          *
TTT ATA ACA GTG TTA CAA TAT GGC AGA CCA CAA TTT AGC TGG CTC GTT
AAA TAT TGT CAC AAT GTT ATA CCG TCT GGT GTT AAA TCG ACC GAG CAA
 F   I   T   V   L   Q   Y   G   R   P   Q   F   S   W   L   V>
   a   a   a   a    TRANSLATION OF FIPV E1 a   a   a   a   a   >

           250        260        270        280
             *          *          *          *
TAT GGC ATT AAA ATG CTG ATC ATG TGG CTA TTA TGG CCT ATT GTT CTA
ATA CCG TAA TTT TAC GAC TAG TAC ACC GAT AAT ACC GGA TAA CAA GAT
 Y   G   I   K   M   L   I   M   W   L   L   W   P   I   V   L>
   a   a   a   a    TRANSLATION OF FIPV E1 a   a   a   a   a   >

290        300        310        320        330
 *          *          *          *          *
GCG CTT ACG ATT TTT AAT GCA TAC TCT GAG TAC CAA GTT TCC AGA TAT
CGC GAA TGC TAA AAA TTA CGT ATG AGA CTC ATG GTT CAA AGG TCT ATA
 A   L   T   I   F   N   A   Y   S   E   Y   Q   V   S   R   Y>
   a   a   a   a    TRANSLATION OF FIPV E1 a   a   a   a   a   >

   340        350        360        370        380
     *          *          *          *          *
GTA ATG TTC GGC TTT AGT GTT GCA GGT GCA GTT GTA ACG TTT GCA CTT
CAT TAC AAG CCG AAA TCA CAA CGT CCA CGT CAA CAT TGC AAA CGT GAA
 V   M   F   G   F   S   V   A   G   A   V   V   T   F   A   L>
   a   a   a   a    TRANSLATION OF FIPV E1 a   a   a   a   a   >
B---------------------------------------------------------------------B
```

FIG. 1C

```
B--------------------------------------------------------------------B
      390         400         410         420         430
       *           *           *           *           *
TGG ATG ATG TAT TTT GTG AGA TCT GTT CAG CTA TAT AGA AGA ACC AAA
ACC TAC TAC ATA AAA CAC TCT AGA CAA GTC GAT ATA TCT TCT TGG TTT

 W   M   M   Y   F   V   R   S   V   Q   L   Y   R   R   T   K>
   a   a   a   a    TRANSLATION OF FIPV E1 a   a   a   a   a   >

          440         450         460         470         480
           *           *           *           *           *
TCA TGG TGG TCT TTT AAT CCT GAG ACT AAT GCA ATT CTT TGT GTT AAT
AGT ACC ACC AGA AAA TTA GGA CTC TGA TTA CGT TAA GAA ACA CAA TTA
 S   W   W   S   F   N   P   E   T   N   A   I   L   C   V   N>
   a   a   a   a    TRANSLATION OF FIPV E1 a   a   a   a   a   >

              490         500         510         520
               *           *           *           *
GCA TTG GGT AGA AGT TAT GTG CTT CCC TTA GAT GGT ACT CCT ACA GGT
CGT AAC CCA TCT TCA ATA CAC GAA GGG AAT CTA CCA TGA GGA TGT CCA
 A   L   G   R   S   Y   V   L   P   L   D   G   T   P   T   G>
   a   a   a   a    TRANSLATION OF FIPV E1 a   a   a   a   a   >

530         540         550         560         570
 *           *           *           *           *
GTT ACC CTT ACT CTA CTT TCA GGA AAT CTA TAT GCT GAA GGT TTC AAA
CAA TGG GAA TGA GAT GAA AGT CCT TTA GAT ATA CGA CTT CCA AAG TTT
 V   T   L   T   L   L   S   G   N   L   Y   A   E   G   F   K>
   a   a   a   a    TRANSLATION OF FIPV E1 a   a   a   a   a   >
C--------------------------------------------------------------------C
```

FIG. 1D

```
C ------------------------------------------------------------------ C
  580         590         600         610         620
    *           *           *           *           *
ATG GCT GGT GGT TTA ACC ATC GAG CAT TTG CCT AAA TAC GTC ATG ATT
TAC CGA CCA CCA AAT TGG TAG CTC GTA AAC GGA TTT ATG CAG TAC TAA
 M   A   G   G   L   T   I   E   H   L   P   K   Y   V   M   I>
  a   a   a   a    TRANSLATION OF FIPV E1 a   a   a   a   a   >

   630         640         650         660         670
     *           *           *           *           *
GCT ACA CCT AGT AGA ACC ATC GTT TAT ACA TTA GTT GGA AAA CAA TTA
CGA TGT GGA TCA TCT TGG TAG CAA ATA TGT AAT CAA CCT TTT GTT AAT
 A   T   P   S   R   T   I   V   Y   T   L   V   G   K   Q   L>
  a   a   a   a    TRANSLATION OF FIPV E1 a   a   a   a   a   >

      680         690         700         710         720
        *           *           *           *           *
AAA GCA ACT ACT GCC ACA GGA TGG GCT TAC TAC GTA AAA TCT AAA GCT
TTT CGT TGA TGA CGG TGT CCT ACC CGA ATG ATG CAT TTT AGA TTT CGA
 K   A   T   T   A   T   G   W   A   Y   Y   V   K   S   K   A>
  a   a   a   a    TRANSLATION OF FIPV E1 a   a   a   a   a   >
D ------------------------------------------------------------------ D
```

```
                 730                 740                 750                 760
                   *                   *                   *                   *
 GGT GAT TAC TCA ACA GAA GCA CGT ACT GAC AAT TTG AGT GAA CAT GAA
 CCA CTA ATG AGT TGT CTT CGT GCA TGA CTG TTA AAC TCA CTT GTA CTT
  G   D   Y   S   T   E   A   R   T   D   N   L   S   E   H   E>
    a   a   a   a    TRANSLATION OF FIPV E1 a   a   a   a   a   >

770                 780
  *                   *
 AAA TTA TTA CAT ATG GTG TAA
 TTT AAT AAT GTA TAC CAC ATT
  K   L   L   H   M   V   *>
    TRANSLATION OF FIPV     >
```

FIG. 2A

```
                10          20          30          40
                 *           *           *           *
ATG GCC ACA CAG GGA CAA CGC GTC AAC TGG GGA GAT GAA CCT TCC AAA
TAC CGG TGT GTC CCT GTT GCG CAG TTG ACC CCT CTA CTT GGA AGG TTT
 M   A   T   Q   G   Q   R   V   N   W   G   D   E   P   S   K>
  a   a   a   a    TRANSLATION OF FIPV N a   a   a   a   a   >

50          60          70          80          90
 *           *           *           *           *
AGA CGT GGT CGT TCT AAC TCT CGT GGT CGG AAG AAT AAT GAT ATA CCT
TCT GCA CCA GCA AGA TTG AGA GCA CCA GCC TTC TTA TTA CTA TAT GGA
 R   R   G   R   S   N   S   R   G   R   K   N   N   D   I   P>
  a   a   a   a    TRANSLATION OF FIPV N a   a   a   a   a   >

   100         110         120         130         140
    *           *           *           *           *
TTG TCA TTC TAC AAC CCC ATT ACC CTC GAA CAA GGA TCT AAA TTT TGG
AAC AGT AAG ATG TTG GGG TAA TGG GAG CTT GTT CCT AGA TTT AAA ACC
 L   S   F   Y   N   P   I   T   L   E   Q   G   S   K   F   W>
  a   a   a   a    TRANSLATION OF FIPV N a   a   a   a   a   >

      150         160         170         180         190
       *           *           *           *           *
AAT TTA TGT CCG AGA GAC CTT GTT CCC AAA GGA ATA GGT AAT AAG GAT
TTA AAT ACA GGC TCT CTG GAA CAA GGG TTT CCT TAT CCA TTA TTC CTA
 N   L   C   P   R   D   L   V   P   K   G   I   G   N   K   D>
  a   a   a   a    TRANSLATION OF FIPV N a   a   a   a   a   >
```

```
A ------------------------------------------------------------------ A
            200                 210                 220                 230                 240
             *                   *                   *                   *                   *
CAA CAA ATT GGT TAT TGG AAT AGA CAG ATT CGT TAT CGT ATT GTA AAA
GTT GTT TAA CCA ATA ACC TTA TCT GTC TAA GCA ATA GCA TAA CAT TTT
 Q   Q   I   G   Y   W   N   R   Q   I   R   Y   R   I   V   K>
   a   a   a   a    TRANSLATION OF FIPV N  a   a   a   a   a   >

                250                 260                 270                 280
                 *                   *                   *                   *
GGC CAG CGT AAG GAA CTC GCT GAG AGG TGG TTC TTT TAC TTC TTA GGT
CCG GTC GCA TTC CTT GAG CGA CTC TCC ACC AAG AAA ATG AAG AAT CCA
 G   Q   R   K   E   L   A   E   R   W   F   F   Y   F   L   G>
   a   a   a   a    TRANSLATION OF FIPV N  a   a   a   a   a   >

290                 300                 310                 320                 330
 *                   *                   *                   *                   *
ACA GGA CCT CAT GCT GAT GCT AAA TTC AAA GAC AAG ATT GAT GGA GTC
TGT CCT GGA GTA CGA CTA CGA TTT AAG TTT CTG TTC TAA CTA CCT CAG
 T   G   P   H   A   D   A   K   F   K   D   K   I   D   G   V>
   a   a   a   a    TRANSLATION OF FIPV N  a   a   a   a   a   >

    340                 350                 360                 370                 380
     *                   *                   *                   *                   *
TTC TGG GTT GCA AGG GAT GGT GCC ATG AAC AAG CCC ACA ACG CTT GGC
AAG ACC CAA CGT TCC CTA CCA CGG TAC TTG TTC GGG TGT TGC GAA CCG
 F   W   V   A   R   D   G   A   M   N   K   P   T   T   L   G>
   a   a   a   a    TRANSLATION OF FIPV N  a   a   a   a   a   >
B ------------------------------------------------------------------ B
```

FIG. 2C

```
B ---------------------------------------------------------------- B

        390        400        410        420        430
         *          *          *          *          *
ACT CGT GGA ACC AAT AAC GAA TCC AAA CCA CTG AGA TTT GAT GGT AAG
TGA GCA CCT TGG TTA TTG CTT AGG TTT GGT GAC TCT AAA CTA CCA TTC

 T   R   G   T   N   N   E   S   K   P   L   R   F   D   G   K>
   a   a   a   a    TRANSLATION OF FIPV N  a   a   a   a   a  >

         440        450        460        470        480
          *          *          *          *          *
ATA CCG CCA CAG TTT CAG CTT GAA GTG AAC CGT TCT AGG AAC AAT TCA
TAT GGC GGT GTC AAA GTC GAA CTT CAC TTG GCA AGA TCC TTG TTA AGT
 I   P   P   Q   F   Q   L   E   V   N   R   S   R   N   N   S>
   a   a   a   a    TRANSLATION OF FIPV N  a   a   a   a   a  >

           490        500        510        520
            *          *          *          *
AGG TCT GGT TCT CAG TCT AGA TCT GTT TCA AGA AAC AGA TCT CAA TCT
TCC AGA CCA AGA GTC AGA TCT AGA CAA AGT TCT TTG TCT AGA GTT AGA
 R   S   G   S   Q   S   R   S   V   S   R   N   R   S   Q   S>
   a   a   a   a    TRANSLATION OF FIPV N  a   a   a   a   a  >

C ---------------------------------------------------------------- C
```

```
C ------------------------------------------------------------ C
530       540       550       560       570
 *         *         *         *         *
AGA GGA AGA CAC CAT TCC AAT AAC CAG AAT AAT AAT GTT GAG GAT ACA
TCT CCT TCT GTG GTA AGG TTA TTG GTC TTA TTA TTA CAA CTC CTA TGT
 R   G   R   H   H   S   N   N   Q   N   N   N   V   E   D   T>
  a   a   a   a   TRANSLATION OF FIPV N  a   a   a   a   a   >

  580       590       600       610       620
   *         *         *         *         *
ATT GTA GCC GTG CTT GAA AAA TTA GGT GTT ACT GAC AAA CAA AGG TCA
TAA CAT CGG CAC GAA CTT TTT AAT CCA CAA TGA CTG TTT GTT TCC AGT
 I   V   A   V   L   E   K   L   G   V   T   D   K   Q   R   S>
  a   a   a   a   TRANSLATION OF FIPV N  a   a   a   a   a   >

    630       640       650       660       670
     *         *         *         *         *
CGT TCT AAA CCT AGA GAA CGT AGT GAT TCC AAA CCT AGG GAC ACA ACA
GCA AGA TTT GGA TCT CTT GCA TCA CTA AGG TTT GGA TCC CTG TGT TGT
 R   S   K   P   R   E   R   S   D   S   K   P   R   D   T   T>
  a   a   a   a   TRANSLATION OF FIPV N  a   a   a   a   a   >

      680       690       700       710       720
       *         *         *         *         *
CCT AAG AAT GCC AAC AAA CAC ACC TGG AAG AAA ACT GCA GGC AAG GGA
GGA TTC TTA CGG TTG TTT GTG TGG ACC TTC TTT TGA CGT CCG TTC CCT
 P   K   N   A   N   K   H   T   W   K   K   T   A   G   K   G>
  a   a   a   a   TRANSLATION OF FIPV N  a   a   a   a   a   >
D ------------------------------------------------------------ D
```

FIG. 2E

```
D ------------------------------------------------------------ D
           730          740          750          760
            *            *            *            *
GAT GTG ACA ACT TTC TAT GGT GCT AGA AGT AGT TCA GCT AAC TTT GGT
CTA CAC TGT TGA AAG ATA CCA CGA TCT TCA TCA AGT CGA TTG AAA CCA
 D   V   T   T   F   Y   G   A   R   S   S   S   A   N   F   G>
   a   a   a   a   TRANSLATION OF FIPV N a   a   a   a   a   >

770          780          790          800          810
 *            *            *            *            *
GAT AGT GAT CTC GTT GCC AAT GGT AAC GCT GCC AAA TGC TAC CCT CAG
CTA TCA CTA GAG CAA CGG TTA CCA TTG CGA CGG TTT ACG ATG GGA GTC
 D   S   D   L   V   A   N   G   N   A   A   K   C   Y   P   Q>
   a   a   a   a   TRANSLATION OF FIPV N a   a   a   a   a   >

   820          830          840          850          860
    *            *            *            *            *
ATA GCT GAA TGT GTT CCA TCA GTG TCT AGC ATA ATC TTT GGC AGT CAA
TAT CGA CTT ACA CAA GGT AGT CAC AGA TCG TAT TAG AAA CCG TCA GTT
 I   A   E   C   V   P   S   V   S   S   I   I   F   G   S   Q>
   a   a   a   a   TRANSLATION OF FIPV N a   a   a   a   a   >

      870          880          890          900          910
       *            *            *            *            *
TGG TCT GCT GAA GAA GCT GGT GAT CAA GTG AAA GTC ACG CTC ACT CAC
ACC AGA CGA CTT CTT CGA CCA CTA GTT CAC TTT CAG TGC GAG TGA GTG
 W   S   A   E   E   A   G   D   Q   V   K   V   T   L   T   H>
   a   a   a   a   TRANSLATION OF FIPV N a   a   a   a   a   >
E ------------------------------------------------------------ E
```

```
          920            930              940              950              960
            *              *                *                *                *
ACC TAC TAC CTG CCA AAG GAT GAT GCC AAA ACT AGT CAA TTC CTA GAA
TGG ATG ATG GAC GGT TTC CTA CTA CGG TTT TGA TCA GTT AAG GAT CTT
 T   Y   Y   L   P   K   D   D   A   K   T   S   Q   F   L   E>
   a   a   a   a    TRANSLATION OF FIPV N  a   a   a   a   a   >

             970            980              990            1000
               *              *                *               *
CAG ATT GAC GCT TAC AAG CGA CCT TCT GAA GTG GCT AAG GAT CAG AGG
GTC TAA CTG CGA ATG TTC GCT GGA AGA CTT CAC CGA TTC CTA GTC TCC
 Q   I   D   A   Y   K   R   P   S   E   V   A   K   D   Q   R>
   a   a   a   a    TRANSLATION OF FIPV N  a   a   a   a   a   >

1010            1020             1030             1040           1050
  *               *                *                *               *
CAA AGA AGA TCC CGT TCT AAG TCT GCT GAT AAG AAG CCT GAG GAG TTG
GTT TCT TCT AGG GCA AGA TTC AGA CGA CTA TTC TTC GGA CTC CTC AAC
 Q   R   R   S   R   S   K   S   A   D   K   K   P   E   E   L>
   a   a   a   a    TRANSLATION OF FIPV N  a   a   a   a   a   >
```

```
F ———————————————————————————————————————————————————————————————— F
 1060         1070         1080         1090         1100
    *            *            *            *            *
TCT GTA ACT CTT GTG GAG GCA TAC ACA GAT GTG TTT GAT GAC ACA CAG
AGA CAT TGA GAA CAC CTC CGT ATG TGT CTA CAC AAA CTA CTG TGT GTC
 S   V   T   L   V   E   A   Y   T   D   V   F   D   D   T   Q>
   a   a   a   a    TRANSLATION OF FIPV N  a   a   a   a   a   >

   1110         1120         1130
      *            *            *
GTT GAG ATG ATT GAT GAG GTT ACG AAC TAA
CAA CTC TAC TAA CTA CTC CAA TGC TTG ATT
 V   E   M   I   D   E   V   T   N   *>
   a    TRANSLATION OF FIPV N  a   a   >
```

FIG. 5A

| | | | | | | |
|---|---|---|---|---|---|---|
| 1 | CGAAAGGGCC | TCGTGATACG | CCTATTTTTA | TAGGTTAATG | TCATGATAAT | AATGGTTTCT |
| 61 | TAGACGTCAG | GTGGCACTTT | TCGGGGAAAT | GTGCGCGGAA | CCCCTATTTG | TTTATTTTTC |
| 121 | TAAATACATT | CAAATATGTA | TCCGCTCATG | AGACAATAAC | CCTGATAAAT | GCTTCAATAA |
| 181 | TATTGAAAAA | GGAAGAGTAT | GAGTATTCAA | CATTTCCGTG | TCGCCCTTAT | TCCCTTTTTT |
| 241 | GCGGCATTTT | GCCTTCCTGT | TTTTGCTCAC | CCAGAAACGC | TGGTGAAAGT | AAAAGATGCT |
| 301 | GAAGATCAGT | TGGGTGCACG | AGTGGGTTAC | ATCGAACTGG | ATCTCAACAG | CGGTAAGATC |
| 361 | CTTGAGAGTT | TTCGCCCCGA | AGAACGTTTT | CCAATGATGA | GCACTTTTAA | AGTTCTGCTA |
| 421 | TGTGGCGCGG | TATTATCCCG | TATTGACGCC | GGGCAAGAGC | AACTCGGTCG | CCGCATACAC |
| 481 | TATTCTCAGA | ATGACTTGGT | TGAGTACTCA | CCAGTCACAG | AAAAGCATCT | TACGGATGGC |
| 541 | ATGACAGTAA | GAGAATTATG | CAGTGCTGCC | ATAACCATGA | GTGATAACAC | TGCGGCCAAC |
| 601 | TTACTTCTGA | CAACGATCGG | AGGACCGAAG | GAGCTAACCG | CTTTTTTGCA | CAACATGGGG |
| 661 | GATCATGTAA | CTCGCCTTGA | TCGTTGGGAA | CCGGAGCTGA | ATGAAGCCAT | ACCAAACGAC |
| 721 | GAGCGTGACA | CCACGATGCC | TGTAGCAATG | GCAACAACGT | TGCGCAAACT | ATTAACTGGC |
| 781 | GAACTACTTA | CTCTAGCTTC | CCGGCAACAA | TTAATAGACT | GGATGGAGGC | GGATAAAGTT |
| 841 | GCAGGACCAC | TTCTGCGCTC | GGCCCTTCCG | GCTGGCTGGT | TTATTGCTGA | TAAATCTGGA |
| 901 | GCCGGTGAGC | GTGGGTCTCG | CGGTATCATT | GCAGCACTGG | GGCCAGATGG | TAAGCCCTCC |
| 961 | CGTATCGTAG | TTATCTACAC | GACGGGGAGT | CAGGCAACTA | TGGATGAACG | AAATAGACAG |
| 1021 | ATCGCTGAGA | TAGGTGCCTC | ACTGATTAAG | CATTGGTAAC | TGTCAGACCA | AGTTTACTCA |
| 1081 | TATATACTTT | AGATTGATTT | AAAACTTCAT | TTTTAATTTA | AAAGGATCTA | GGTGAAGATC |
| 1141 | CTTTTTGATA | ATCTCATGAC | CAAAATCCCT | TAACGTGAGT | TTTCGTTCCA | CTGAGCGTCA |
| 1201 | GACCCCGTAG | AAAAGATCAA | AGGATCTTCT | TGAGATCCTT | TTTTTCTGCG | CGTAATCTGC |
| 1261 | TGCTTGCAAA | CAAAAAAACC | ACCGCTACCA | GCGGTGGTTT | GTTTGCCGGA | TCAAGAGCTA |
| 1321 | CCAACTCTTT | TTCCGAAGGT | AACTGGCTTC | AGCAGAGCGC | AGATACCAAA | TACTGTCCTT |
| 1381 | CTAGTGTAGC | CGTAGTTAGG | CCACCACTTC | AAGAACTCTG | TAGCACCGCC | TACATACCTC |
| 1441 | GCTCTGCTAA | TCCTGTTACC | AGTGGCTGCT | GCCAGTGGCG | ATAAGTCGTG | TCTTACCGGG |
| 1501 | TTGGACTCAA | GACGATAGTT | ACCGGATAAG | GCGCAGCGGT | CGGGCTGAAC | GGGGGGTTCG |

| | | | | | | |
|---|---|---|---|---|---|---|
| 1561 | TGCACACAGC | CCAGCTTGGA | GCGAACGACC | TACACCGAAC | TGAGATACCT | ACAGCGTGAG |
| 1621 | CATTGAGAAA | GCGCCACGCT | TCCCGAAGGG | AGAAAGGCGG | ACAGGTATCC | GGTAAGCGGC |
| 1681 | AGGGTCGGAA | CAGGAGAGCG | CACGAGGGAG | CTTCCAGGGG | GAAACGCCTG | GTATCTTTAT |
| 1741 | AGTCCTGTCG | GGTTTCGCCA | CCTCTGACTT | GAGCGTCGAT | TTTTGTGATG | CTCGTCAGGG |
| 1801 | GGGCGGAGCC | TATGGAAAAA | CGCCAGCAAC | GCGGCCTTTT | TACGGTTCCT | GGCCTTTTGC |
| 1861 | TGGCCTTTTG | CTCACATGTT | CTTTCCTGCG | TTATCCCCTG | ATTCTGTGGA | TAACCGTATT |
| 1921 | ACCGCCTTTG | AGTGAGCTGA | TACCGCTCGC | CGCAGCCGAA | CGACCGAGCG | CAGCGAGTCA |
| 1981 | GTGAGCGAGG | AAGCGGAAGA | GCGCCCAATA | CGCAAACCGC | CTCTCCCCGC | GCGTTGGCCG |
| 2041 | ATTCATTAAT | GCAGCTGGCA | CGACAGGTTT | CCCGACTGGA | AAGCGGGCAG | TGAGCGCAAC |
| 2101 | GCAATTAATG | TGAGTTAGCT | CACTCATTAG | GCACCCCAGG | CTTTACACTT | TATGCTTCCG |
| 2161 | GCTCGTATGT | TGTGTGGAAT | TGTGAGCGGA | TAACAATTTC | ACACAGGAAA | CAGCTATGAC |
| 2221 | CATGATTACG | CCAAGCTTTT | GCGATCAATA | AATGGATCAC | AACCAGTATC | TCTTAACGAT |
| 2281 | GTTCTTCGCA | GATGATGATT | CATTTTTTAA | GTATTTGGCT | AGTCAAGATG | ATGAAATCTT |
| 2341 | CATTATCTGA | TATATTGCAA | ATCACTCAAT | ATCTAGACTT | TCTGTTATTA | TTATTGATCC |
| 2401 | AATCAAAAAA | TAAATTAGAA | GCCGTGGGTC | ATTGTTATGA | ATCTCTTTCA | GAGGAATACA |
| 2461 | GACAATTGAC | AAAATTCACA | GACTTTCAAG | ATTTTAAAAA | ACTGTTTAAC | AAGGTCCCTA |
| 2521 | TTGTTACAGA | TGGAAGGGTC | AAACTTAATA | AAGGATATTT | GTTCGACTTT | GTGATTAGTT |
| 2581 | TGATGCGATT | CAAAAAAGAA | TCCTCTCTAG | CTACCACCGC | AATAGATCCT | GTTAGATACA |
| 2641 | TAGATCCTCG | TCGCAATATC | GCATTTTCTA | ACGTGATGGA | TATATTAAAG | TCGAATAAAG |
| 2701 | TGAACAATAA | TTAATTCTTT | ATTGTCATCA | TGAACGGCGG | ACATATTCAG | TTGATAATCG |
| 2761 | GCCCCATGTT | TTCAGGTAAA | AGTACAGAAT | TAATTAGACG | AGTTAGACGT | TATCAAATAG |
| 2821 | CTCAATATAA | ATGCGTGACT | ATAAAATATT | CTAACGATAA | TAGATACGGA | ACGGGACTAT |
| 2881 | GGACGCATGA | TAAGAATAAT | TTTGAAGCAT | TGGAAGCAAC | TAAACTATGT | GATCTCTTGG |
| 2941 | AATCAATTAC | AGATTTCTCC | GTGATAGGTA | TCGATGAAGG | ACAGTTCTTT | CCAGACATTG |
| 3001 | TTGAATTCCG | AGCTTGGCTG | CAGGTCGGGG | ATCCCCCCTG | CCCGGTTATT | ATTATTTTTG |

```
3061 ACACCAGACC AACTGGTAAT GGTAGCGAAC GGCGCTCAGC TGAATTCCGC CGATACTGAC
3121 GGGCTCCAGG AGTCGTCGCC ACCAATCCCC ATATGGAAAC CGTCGATATT CAGCCATGTG
3181 CCTTCTTCCG CGTGCAGCAG ATGGCGATGG CTGGTTTCCA TCAGTTGCTG TTGACTGTAG
3241 CGGCTGATGT TGAACTGGAA GTCGCCGCGC CACTGGTGTG GGCCATAATT CAATTCGCGC
3301 GTCCCGCAGC GCAGACCGTT TTCGCTCGGG AAGACGTACG GGGTATACAT GTCTGACAAT
3361 GGCAGATCCC AGCGGTCAAA ACAGGCGGCA GTAAGGCGGT CGGGATAGTT TTCTTGCGGC
3421 CCTAATCCGA GCCAGTTTAC CCGCTCTGCT ACCTGCGCCA GCTGGCAGTT CAGGCCAATC
3481 CGCGCCGGAT GCGGTGTATC GCTCGCCACT TCAACATCAA CGGTAATCGC CATTTGACCA
3541 CTACCATCAA TCCGGTAGGT TTTCCGGCTG ATAAATAAGG TTTTCCCCTG ATGCTGCCAC
3601 GCGTGACCGG TCGTAATCAG CACCGCATCA GCAAGTGTAT CTGCCGTGCA CTGCAACAAC
3661 GCTGCTTCGG CCTGGTAATG GCCCGCCGCC TTCCAGCGTT CGACCCAGGC GTTAGGGTCA
3721 ATGCGGGTCG CTTCACTTAC GCCAATGTCG TTATCCAGCG GTGCACGGGT GAACTGATCG
3781 CGCAGCGGCG TCAGCAGTTG TTTTTTATCG CCAATCCACA TCTGTGAAAG AAAGCCTGAC
3841 TGGCGGTTAA ATTGCCAACG CTTATTACCC AGCTCGATGC AAAAATCCAT TTCGCTGGTG
3901 GTCAGATGCG GGATGGCGTG GGACGCGGCG GGGAGCGTCA CACTGAGGTT TTCCGCCAGA
3961 CGCCACTGCT GCCAGGCGCT GATGTGCCCG GCTTCTGACC ATGCGGTCGC GTTCGGTTGC
4021 ACTACGCGTA CTGTGAGCCA GAGTTGCCCG GCGCTCTCCG GCTGCGGTAG TTCAGGCAGT
4081 TCAATCAACT GTTTACCTTG TGGAGCGACA TCCAGAGGCA CTTCACCGCT TGCCAGCGGC
4141 TTACCATCCA GCGCCACCAT CCAGTGCAGG AGCTCGTTAT CGCTATGACG GAACAGGTAT
4201 TCGCTGGTCA CTTCGATGGT TTGCCCGGAT AAACGGAACT GGAAAAACTG CTGCTGGTGT
4261 TTTGCTTCCG TCAGCGCTGG ATGCGGCGTG CGGTCGGCAA AGACCAGACC GTTCATACAG
4321 AACTGGCGAT CGTTCGGCGT ATCGCCAAAA TCACCGCCGT AAGCCGACCA CGGGTTGCCG
4381 TTTTCATCAT ATTTAATCAG CGACTGATCC ACCCAGTCCC AGACGAAGCC GCCCTGTAAA
4441 CGGGGATACT GACGAAACGC CTGCCAGTAT TTAGCGAAAC CGCCAAGACT GTTACCCATC
4501 GCGTGGGCGT ATTCGCAAAG GATCAGCGGG CGCGTCTCTC CAGGTAGCGA AAGCCATTTT
4561 TTGATGGACC ATTTCGGCAC AGCCGGGAAG GGCTGGTCTT CATCCACGCG CGCGTACATC
```

| | | | | | | |
|---|---|---|---|---|---|---|
| 4621 | GGGCAAATAA | TATCGGTGGC | CGTGGTGTCG | GCTCCGCCGC | CTTCATACTG | CACCGGGCGG |
| 4681 | GAAGGATCGA | CAGATTTGAT | CCAGCGATAC | AGCGCGTCGT | GATTAGCGCC | GTGGCCTGAT |
| 4741 | TCATTCCCCA | GCGACCAGAT | GATCACACTC | GGGTGATTAC | GATCGCGCTG | CACCATTCGC |
| 4801 | GTTACGCGTT | CGCTCATCGC | CGGTAGCCAG | CGCGGATCAT | CGGTCAGACG | ATTGATTGGC |
| 4861 | ACCATGCCGT | GGGTTTCAAT | ATTGGCTTCA | TCCACCACAT | ACAGGCCGTA | GCGGTCGCAC |
| 4921 | AGCGTGTACC | ACAGCGGATG | GTTCGGATAA | TGCGAACAGC | GCACGGCGTT | AAAGTTGTTC |
| 4981 | TGCTTCATCA | GCAGGATATC | CTGCACCATC | GTCTGCTCAT | CCATGACCTG | ACCATGCAGA |
| 5041 | GGATGATGCT | CGTGACGGTT | AACGCCTCGA | ATCAGCAACG | GCTTGCCGTT | CAGCAGCAGC |
| 5101 | AGACCATTTT | CAATCCGCAC | CTCGCGGAAA | CCGACATCGC | AGGCTTCTGC | TTCAATCAGC |
| 5161 | GTGCCGTCGG | CGGTGTGCAG | TTCAACCACC | GCACGATAGA | GATTCGGGAT | TTCGGCGCTC |
| 5221 | CACAGTTTCG | GGTTTTCGAC | CTTGAGACGT | AGTGTGACGC | GATCGGCATA | ACCACCACGC |
| 5281 | TCATCGATAA | TTTCACCGCC | GAAAGGCGCG | GTGCCGCTGG | CGACCTGCGT | TTCACCCTGC |
| 5341 | CATAAAGAAA | CTGTTACCCG | TAGGTAGTCA | CGCAACTCGC | CGCACATCTG | AACTTCAGCC |
| 5401 | TCCAGTACAG | CGCGGCTGAA | ATCATCATTA | AAGCGAGTGG | CAACATGGAA | ATCGCTGATT |
| 5461 | TGTGTAGTCG | GTTTATGCAG | CAACGAGACG | TCACGGAAAA | TGCCGCTCAT | CCGCCACATA |
| 5521 | TCCTGATCTT | CCAGATAACT | GCCGTCACTC | CAACGCAGCA | CCATCACCGC | GAGGCGGTTT |
| 5581 | TCTCCGGCGC | GTAAAAATGC | GCTCAGGTCA | AATTCAGACG | GCAAACGACT | GTCCTGGCCG |
| 5641 | TAACCGACCC | AGCGCCCGTT | GCACCACAGA | TGAAACGCCG | AGTTAACGCC | ATCAAAAATA |
| 5701 | ATTCGCGTCT | GGCCTTCCTG | TAGCCAGCTT | TCATCAACAT | TAAATGTGAG | CGAGTAACAA |
| 5761 | CCCGTCGGAT | TCTCCGTGGG | AACAAACGGC | GGATTGACCG | TAATGGGATA | GGTTACGTTG |
| 5821 | GTGTAGATGG | GCGCATCGTA | ACCGTGCATC | TGCCAGTTTG | AGGGGACGAC | GACAGTATCG |
| 5881 | GCCTCAGGAA | GATCGCACTC | CAGCCAGCTT | TCCGGCACCG | CTTCTGGTGC | CGGAAACCAG |
| 5941 | GCAAAGCGCC | ATTCGCCATT | CAGGCTGCGC | AACTGTTGGG | AAGGGCGATC | GGTGCGGGCC |
| 6001 | TCTTCGCTAT | TACGCCAGCT | GGCGAAAGGG | GGATGTGCTG | CAAGGCGATT | AAGTTGGGTA |
| 6061 | ACGCCAGGGT | TTTCCCAGTC | ACGACGTTGT | AAAACGACGG | GATCCCTCGA | GGAATTCATT |

6121 TATAGCATAG AAAAAAACAA AATGAAATTC TACTATATTT TTACATACAT ATATTCTAAA
6181 TATGAAAGTG GTGATTGTGA CTAGCGTAGC ATCGCTTCTA GACATATACT ATATAGTAAT
6241 ACCAATACTC AAGACTACGA AACTGATACA ATCTCTTATC ATGTGGGTAA TGTTCTCGAT
6301 GTCGAATAGC CATATGCCGG TAGTTGCGAT ATACATAAAC TGATCACTAA TTCCAAACCC
6361 ACCCGCTTTT TATAGTAAGT TTTTCACCCA TAAATAATAA ATACAATAAT TAATTTCTCG
6421 TAAAAGTAGA AAATATATTC TAATTTATTG CACGGTAAGG AAGTAGAATC ATAAAGAACA
6481 GTGACGGATC CCAATTCGGG CATTTTTGGT TTGAACTAAA CAAAATGAAG TACATTTTGC
6541 TAATACTCGC GTGCATAATT GCATGCGTTT ATGGTGAACG CTACTGTGCC ATGCAAGACA
6601 GTGGCTTGCA GTGTATTAAT GGCACAAATT CAAGATGTCA AACCTGCTTT GAACGTGGTG
6661 ATCTTATTTG GCATCTTGCT AACTGGAACT TCAGCTGGTC TGTAATATTG ATTGTTTTTA
6721 TAACAGTGTT ACAATATGGC AGACCACAAT TTAGCTGGCT CGTTTATGGC ATTAAAATGC
6781 TGATCATGTG GCTATTATGG CCTATTGTTC TAGCGCTTAC GATTTTTAAT GCATACTCTG
6841 AGTACCAAGT TTCCAGATAT GTAATGTTCG GCTTTAGTGT TGCAGGTGCA GTTGTAACGT
6901 TTGCACTTTG GATGATGTAT TTTGTGAGAT CTGTTCAGCT ATATAGAAGA ACCAAATCAT
6961 GGTGGTCTTT TAATCCTGAG ACTAATGCAA TTCTTTGTGT TAATGCATTG GGTAGAAGTT
7021 ATGTGCTTCC CTTAGATGGT ACTCCTACAG GTGTTACCCT TACTCTACTT TCAGGAAATC
7081 TATATGCTGA AGGTTTCAAA ATGGCTGGTG GTTTAACCAT CGAGCATTTG CCTAAATACG
7141 TCATGATTGC TACACCTAGT AGAACCATCG TTTATACATT AGTTGGAAAA CAATTAAAAG
7201 CAACTACTGC CACAGGATGG GCTTACTACG TAAAATCTAA AGCTGGTGAT TACTCAACAG
7261 AAGCACGTAC TGACAATTTG AGTGAACATG AAAAATTATT ACATATGGTG TAACTAAACT
7321 TTCAAATGGG GGAATTCTGT GAGCGTATGG CAAACGAAGG AAAAATTAGT TATAGTAGCC
7381 GCACTCGATG GGACATTTCA ACGTAAACCG TTTAATAATA TTTTGAATCT TATTCCATTA
7441 TCTGAAATGG TGGTAAAACT AACTGCTGTG TGTATGAAAT GCTTTAAGGA GGCTTCCTTT
7501 TCTAAACGAT TGGGTGAGGA AACCGAGATA GAAATAATAG GAGGTAATGA TATGTATCAA
7561 TCGGTGTGTA GAAAGTGTTA CATCGACTCA TAATATTATA TTTTTTATCT AAAAAACTAA

```
7621 AAATAAACAT TGATTAAATT TTAATATAAT ACTTAAAAAT GGATGTTGTG TCGTTAGATA
7681 AACCGTTTAT GTATTTTGAG GAAATTGATA ATGAGTTAGA TTACGAACCA GAAAGTGCAA
7741 ATGAGGTCGC AAAAAAACTG CCGTATCAAG GACAGTTAAA ACTATTACTA GGAGAATTAT
7801 TTTTTCTTAG TAAGTTACAG CGACACGGTA TATTAGATGG TGCCACCGTA GTGTATATAG
7861 GATCTGCTCC CGGTACACAT ATACGTTATT TGAGAGATCA TTTCTATAAT TTAGGAGTGA
7921 TCATCAAATG GATGCTAATT GACGGCCGCC ATCATGATCC TATTTTAAAT GGATTGCGTG
7981 ATGTGACTCT AGTGACTCGG TTCGTTGATG AGGAATATCT ACGATCCATC AAAAAACAAC
8041 TGCATCCTTC TAAGATTATT TTAATTTCTG ATGTGAGATC CAAACGAGGA GGAAATGAAC
8101 CTAGTACGGC GGATTTACTA AGTAATTACG CTCTACAAAA TGTCATGATT AGTATTTTAA
8161 ACCCCGTGGC GTCTAGTCTT AAATGGAGAT GCCCGTTTCC AGATCAATGG ATCAAGGACT
8221 TTTATATCCC ACACGGTAAT AAAATGTTAC AACCTTTTGC TCCTTCATAT TCAGGGCCGT
8281 CGTTTTACAA CGTCGTGACT GGGAAAACCC TGGCGTTACC CAACTTAATC GCCTTGCAGC
8341 ACATCCCCCT TTCGCCAGCT GGCGTAATAG CGAAGAGGCC CGCACCGATC GCCCTTCCCA
8401 ACAGTTGCGC AGCCTGAATG GCGAATGGCG CCTGATGCGG TATTTTCTCT TTACGCATCT
8461 GTGCGGTATT TCACACCGCA TATGGTGCAC TCTCAGTACC ATCTGCTCTG ATGCCGCATA
8521 GTTAAGCCAG TACACTCCGC TATCGCTACG TGACTGGGTC ATGGCTGCGC CCCGACACCC
8581 GCCAACACCC GCTGACGCGC CCTGACGGGC TTGTCTGCTC CCGGCATCCG CTTACAGACA
8641 AGCTGTGACC GTCTCCGGGA GCTGCATGTG TCAGAGGTTT TCACCGTCAT CACCGAAACG
8701 CGCGAGGCAG
```

FIG. 6A

```
   1 CGAAAGGGCC TCGTGATACG CCTATTTTTA TAGGTTAATG TCATGATAAT AATGGTTTCT
  61 TAGACGTCAG GTGGCACTTT TCGGGGAAAT GTGCGCGGAA CCCCTATTTG TTTATTTTTC
 121 TAAATACATT CAAATATGTA TCCGCTCATG AGACAATAAC CCTGATAAAT GCTTCAATAA
 181 TATTGAAAAA GGAAGAGTAT GAGTATTCAA CATTTCCGTG TCGCCCTTAT TCCCTTTTTT
 241 GCGGCATTTT GCCTTCCTGT TTTTGCTCAC CCAGAAACGC TGGTGAAAGT AAAAGATGCT
 301 GAAGATCAGT TGGGTGCACG AGTGGGTTAC ATCGAACTGG ATCTCAACAG CGGTAAGATC
 361 CTTGAGAGTT TTCGCCCCGA AGAACGTTTT CCAATGATGA GCACTTTTAA AGTTCTGCTA
 421 TGTGGCGCGG TATTATCCCG TATTGACGCC GGGCAAGAGC AACTCGGTCG CCGCATACAC
 481 TATTCTCAGA ATGACTTGGT TGAGTACTCA CCAGTCACAG AAAAGCATCT TACGGATGGC
 541 ATGACAGTAA GAGAATTATG CAGTGCTGCC ATAACCATGA GTGATAACAC TGCGGCCAAC
 601 TTACTTCTGA CAACGATCGG AGGACCGAAG GAGCTAACCG CTTTTTTGCA CAACATGGGG
 661 GATCATGTAA CTCGCCTTGA TCGTTGGGAA CCGGAGCTGA ATGAAGCCAT ACCAAACGAC
 721 GAGCGTGACA CCACGATGCC TGTAGCAATG GCAACAACGT TGCGCAAACT ATTAACTGGC
 781 GAACTACTTA CTCTAGCTTC CCGGCAACAA TTAATAGACT GGATGGAGGC GGATAAAGTT
 841 GCAGGACCAC TTCTGCGCTC GGCCCTTCCG GCTGGCTGGT TTATTGCTGA TAAATCTGGA
 901 GCCGGTGAGC GTGGGTCTCG CGGTATCATT GCAGCACTGG GGCCAGATGG TAAGCCCTCC
 961 CGTATCGTAG TTATCTACAC GACGGGGAGT CAGGCAACTA TGGATGAACG AAATAGACAG
1021 ATCGCTGAGA TAGGTGCCTC ACTGATTAAG CATTGGTAAC TGTCAGACCA AGTTTACTCA
1081 TATATACTTT AGATTGATTT AAAACTTCAT TTTTAATTTA AAAGGATCTA GGTGAAGATC
1141 CTTTTTGATA ATCTCATGAC CAAAATCCCT TAACGTGAGT TTTCGTTCCA CTGAGCGTCA
1201 GACCCCGTAG AAAAGATCAA AGGATCTTCT TGAGATCCTT TTTTTCTGCG CGTAATCTGC
1261 TGCTTGCAAA CAAAAAAACC ACCGCTACCA GCGGTGGTTT GTTTGCCGGA TCAAGAGCTA
1321 CCAACTCTTT TTCCGAAGGT AACTGGCTTC AGCAGAGCGC AGATACCAAA TACTGTCCTT
1381 CTAGTGTAGC CGTAGTTAGG CCACCACTTC AAGAACTCTG TAGCACCGCC TACATACCTC
1441 GCTCTGCTAA TCCTGTTACC AGTGGCTGCT GCCAGTGGCG ATAAGTCGTG TCTTACCGGG
1501 TTGGACTCAA GACGATAGTT ACCGGATAAG GCGCAGCGGT CGGGCTGAAC GGGGGGTTCG
```

| | | | | | | |
|---|---|---|---|---|---|---|
| 1561 | TGCACACAGC | CCAGCTTGGA | GCGAACGACC | TACACCGAAC | TGAGATACCT | ACAGCGTGAG |
| 1621 | CATTGAGAAA | GCGCCACGCT | TCCCGAAGGG | AGAAAGGCGG | ACAGGTATCC | GGTAAGCGGC |
| 1681 | AGGGTCGGAA | CAGGAGAGCG | CACGAGGGAG | CTTCCAGGGG | GAAACGCCTG | GTATCTTTAT |
| 1741 | AGTCCTGTCG | GGTTTCGCCA | CCTCTGACTT | GAGCGTCGAT | TTTTGTGATG | CTCGTCAGGG |
| 1801 | GGGCGGAGCC | TATGGAAAAA | CGCCAGCAAC | GCGGCCTTTT | TACGGTTCCT | GGCCTTTTGC |
| 1861 | TGGCCTTTTG | CTCACATGTT | CTTTCCTGCG | TTATCCCCTG | ATTCTGTGGA | TAACCGTATT |
| 1921 | ACCGCCTTTG | AGTGAGCTGA | TACCGCTCGC | CGCAGCCGAA | CGACCGAGCG | CAGCGAGTCA |
| 1981 | GTGAGCGAGG | AAGCGGAAGA | GCGCCCAATA | CGCAAACCGC | CTCTCCCCGC | GCGTTGGCCG |
| 2041 | ATTCATTAAT | GCAGCTGGCA | CGACAGGTTT | CCCGACTGGA | AAGCGGGCAG | TGAGCGCAAC |
| 2101 | GCAATTAATG | TGAGTTAGCT | CACTCATTAG | GCACCCCAGG | CTTTACACTT | TATGCTTCCG |
| 2161 | GCTCGTATGT | TGTGTGGAAT | TGTGAGCGGA | TAACAATTTC | ACACAGGAAA | CAGCTATGAC |
| 2221 | CATGATTACG | CCAAGCTTTT | GCGATCAATA | AATGGATCAC | AACCAGTATC | TCTTAACGAT |
| 2281 | GTTCTTCGCA | GATGATGATT | CATTTTTTAA | GTATTTGGCT | AGTCAAGATG | ATGAAATCTT |
| 2341 | CATTATCTGA | TATATTGCAA | ATCACTCAAT | ATCTAGACTT | TCTGTTATTA | TTATTGATCC |
| 2401 | AATCAAAAAA | TAAATTAGAA | GCCGTGGGTC | ATTGTTATGA | ATCTCTTTCA | GAGGAATACA |
| 2461 | GACAATTGAC | AAAATTCACA | GACTTTCAAG | ATTTTAAAAA | ACTGTTTAAC | AAGGTCCCTA |
| 2521 | TTGTTACAGA | TGGAAGGGTC | AAACTTAATA | AAGGATATTT | GTTCGACTTT | GTGATTAGTT |
| 2581 | TGATGCGATT | CAAAAAAGAA | TCCTCTCTAG | CTACCACCGC | AATAGATCCT | GTTAGATACA |
| 2641 | TAGATCCTCG | TCGCAATATC | GCATTTTCTA | ACGTGATGGA | TATATTAAAG | TCGAATAAAG |
| 2701 | TGAACAATAA | TTAATTCTTT | ATTGTCATCA | TGAACGGCGG | ACATATTCAG | TTGATAATCG |
| 2761 | GCCCCATGTT | TTCAGGTAAA | AGTACAGAAT | TAATTAGACG | AGTTAGACGT | TATCAAATAG |
| 2821 | CTCAATATAA | ATGCGTGACT | ATAAAATATT | CTAACGATAA | TAGATACGGA | ACGGGACTAT |
| 2881 | GGACGCATGA | TAAGAATAAT | TTTGAAGCAT | TGGAAGCAAC | TAAACTATGT | GATCTCTTGG |
| 2941 | AATCAATTAC | AGATTTCTCC | GTGATAGGTA | TCGATGAAGG | ACAGTTCTTT | CCAGACATTG |
| 3001 | TTGAATTCCG | AGCTTGGCTG | CAGGTCGGGG | ATCCCCCCTG | CCCGGTTATT | ATTATTTTTG |

```
3061 ACACCAGACC AACTGGTAAT GGTAGCGAAC GGCGCTCAGC TGAATTCCGC CGATACTGAC
3121 GGGCTCCAGG AGTCGTCGCC ACCAATCCCC ATATGGAAAC CGTCGATATT CAGCCATGTG
3181 CCTTCTTCCG CGTGCAGCAG ATGGCGATGG CTGGTTTCCA TCAGTTGCTG TTGACTGTAG
3241 CGGCTGATGT TGAACTGGAA GTCGCCGCGC CACTGGTGTG GGCCATAATT CAATTCGCGC
3301 GTCCCGCAGC GCAGACCGTT TTCGCTCGGG AAGACGTACG GGGTATACAT GTCTGACAAT
3361 GGCAGATCCC AGCGGTCAAA ACAGGCGGCA GTAAGGCGGT CGGGATAGTT TTCTTGCGGC
3421 CCTAATCCGA GCCAGTTTAC CCGCTCTGCT ACCTGCGCCA GCTGGCAGTT CAGGCCAATC
3481 CGCGCCGGAT GCGGTGTATC GCTCGCCACT TCAACATCAA CGGTAATCGC CATTTGACCA
3541 CTACCATCAA TCCGGTAGGT TTTCCGGCTG ATAAATAAGG TTTTCCCCTG ATGCTGCCAC
3601 GCGTGACCGG TCGTAATCAG CACCGCATCA GCAAGTGTAT CTGCCGTGCA CTGCAACAAC
3661 GCTGCTTCGG CCTGGTAATG GCCCGCCGCC TTCCAGCGTT CGACCCAGGC GTTAGGGTCA
3721 ATGCGGGTCG CTTCACTTAC GCCAATGTCG TTATCCAGCG GTGCACGGGT GAACTGATCG
3781 CGCAGCGGCG TCAGCAGTTG TTTTTTATCG CCAATCCACA TCTGTGAAAG AAAGCCTGAC
3841 TGGCGGTTAA ATTGCCAACG CTTATTACCC AGCTCGATGC AAAAATCCAT TTCGCTGGTG
3901 GTCAGATGCG GGATGGCGTG GGACGCGGCG GGGAGCGTCA CACTGAGGTT TTCCGCCAGA
3961 CGCCACTGCT GCCAGGCGCT GATGTGCCCG GCTTCTGACC ATGCGGTCGC GTTCGGTTGC
4021 ACTACGCGTA CTGTGAGCCA GAGTTGCCCG GCGCTCTCCG GCTGCGGTAG TTCAGGCAGT
4081 TCAATCAACT GTTTACCTTG TGGAGCGACA TCCAGAGGCA CTTCACCGCT TGCCAGCGGC
4141 TTACCATCCA GCGCCACCAT CCAGTGCAGG AGCTCGTTAT CGCTATGACG GAACAGGTAT
4201 TCGCTGGTCA CTTCGATGGT TTGCCCGGAT AAACGGAACT GGAAAAACTG CTGCTGGTGT
4261 TTTGCTTCCG TCAGCGCTGG ATGCGGCGTG CGGTCGGCAA AGACCAGACC GTTCATACAG
4321 AACTGGCGAT CGTTCGGCGT ATCGCCAAAA TCACCGCCGT AAGCCGACCA CGGGTTGCCG
4381 TTTTCATCAT ATTTAATCAG CGACTGATCC ACCCAGTCCC AGACGAAGCC GCCCTGTAAA
4441 CGGGGATACT GACGAAACGC CTGCCAGTAT TTAGCGAAAC CGCCAAGACT GTTACCCATC
4501 GCGTGGGCGT ATTCGCAAAG GATCAGCGGG CGCGTCTCTC CAGGTAGCGA AAGCCATTTT
```

| | | | | | | |
|---|---|---|---|---|---|---|
| 4561 | TTGATGGACC | ATTTCGGCAC | AGCCGGGAAG | GGCTGGTCTT | CATCCACGCG | CGCGTACATC |
| 4621 | GGGCAAATAA | TATCGGTGGC | CGTGGTGTCG | GCTCCGCCGC | CTTCATACTG | CACCGGGCGG |
| 4681 | GAAGGATCGA | CAGATTTGAT | CCAGCGATAC | AGCGCGTCGT | GATTAGCGCC | GTGGCCTGAT |
| 4741 | TCATTCCCCA | GCGACCAGAT | GATCACACTC | GGGTGATTAC | GATCGCGCTG | CACCATTCGC |
| 4801 | GTTACGCGTT | CGCTCATCGC | CGGTAGCCAG | CGCGGATCAT | CGGTCAGACG | ATTGATTGGC |
| 4861 | ACCATGCCGT | GGGTTTCAAT | ATTGGCTTCA | TCCACCACAT | ACAGGCCGTA | GCGGTCGCAC |
| 4921 | AGCGTGTACC | ACAGCGGATG | GTTCGGATAA | TGCGAACAGC | GCACGGCGTT | AAAGTTGTTC |
| 4981 | TGCTTCATCA | GCAGGATATC | CTGCACCATC | GTCTGCTCAT | CCATGACCTG | ACCATGCAGA |
| 5041 | GGATGATGCT | CGTGACGGTT | AACGCCTCGA | ATCAGCAACG | GCTTGCCGTT | CAGCAGCAGC |
| 5101 | AGACCATTTT | CAATCCGCAC | CTCGCGGAAA | CCGACATCGC | AGGCTTCTGC | TTCAATCAGC |
| 5161 | GTGCCGTCGG | CGGTGTGCAG | TTCAACCACC | GCACGATAGA | GATTCGGGAT | TTCGGCGCTC |
| 5221 | CACAGTTTCG | GGTTTTCGAC | CTTGAGACGT | AGTGTGACGC | GATCGGCATA | ACCACCACGC |
| 5281 | TCATCGATAA | TTTCACCGCC | GAAAGGCGCG | GTGCCGCTGG | CGACCTGCGT | TTCACCCTGC |
| 5341 | CATAAAGAAA | CTGTTACCCG | TAGGTAGTCA | CGCAACTCGC | CGCACATCTG | AACTTCAGCC |
| 5401 | TCCAGTACAG | CGCGGCTGAA | ATCATCATTA | AAGCGAGTGG | CAACATGGAA | ATCGCTGATT |
| 5461 | TGTGTAGTCG | GTTTATGCAG | CAACGAGACG | TCACGGAAAA | TGCCGCTCAT | CCGCCACATA |
| 5521 | TCCTGATCTT | CCAGATAACT | GCCGTCACTC | CAACGCAGCA | CCATCACCGC | GAGGCGGTTT |
| 5581 | TCTCCGGCGC | GTAAAAATGC | GCTCAGGTCA | AATTCAGACG | GCAAACGACT | GTCCTGGCCG |
| 5641 | TAACCGACCC | AGCGCCCGTT | GCACCACAGA | TGAAACGCCG | AGTTAACGCC | ATCAAAAATA |
| 5701 | ATTCGCGTCT | GGCCTTCCTG | TAGCCAGCTT | TCATCAACAT | TAAATGTGAG | CGAGTAACAA |
| 5761 | CCCGTCGGAT | TCTCCGTGGG | AACAAACGGC | GGATTGACCG | TAATGGGATA | GGTTACGTTG |
| 5821 | GTGTAGATGG | GCGCATCGTA | ACCGTGCATC | TGCCAGTTTG | AGGGGACGAC | GACAGTATCG |
| 5881 | GCCTCAGGAA | GATCGCACTC | CAGCCAGCTT | TCCGGCACCG | CTTCTGGTGC | CGGAAACCAG |
| 5941 | GCAAAGCGCC | ATTCGCCATT | CAGGCTGCGC | AACTGTTGGG | AAGGGCGATC | GGTGCGGGCC |
| 6001 | TCTTCGCTAT | TACGCCAGCT | GGCGAAAGGG | GGATGTGCTG | CAAGGCGATT | AAGTTGGGTA |
| 6061 | ACGCCAGGGT | TTTCCCAGTC | ACGACGTTGT | AAAACGACGG | GATCCCTCGA | GGAATTCATT |

6121 TATAGCATAG AAAAAAACAA AATGAAATTC TACTATATTT TTACATACAT ATATTCTAAA
6181 TATGAAAGTG GTGATTGTGA CTAGCGTAGC ATCGCTTCTA GACATATACT ATATAGTAAT
6241 ACCAATACTC AAGACTACGA AACTGATACA ATCTCTTATC ATGTGGGTAA TGTTCTCGAT
6301 GTCGAATAGC CATATGCCGG TAGTTGCGAT ATACATAAAC TGATCACTAA TTCCAAACCC
6361 ACCCGCTTTT TATAGTAAGT TTTTCACCCA TAAATAATAA ATACAATAAT TAATTTCTCG
6421 TAAAAGTAGA AAATATATTC TAATTTATTG CACGGTAAGG AAGTAGAATC ATAAAGAACA
6481 GTGACGGATC CCGGGATGGC CACACAGGGA CAACGCGTCA ACTGGGGAGA TGAACCTTCC
6541 AAAAGACGTG GTCGTTCTAA CTCTCGTGGT CGGAAGAATA ATGATATACC TTTGTCATTC
6601 TACAACCCCA TTACCCTCGA ACAAGGATCT AAATTTTGGA ATTTATGTCC GAGAGACCTT
6661 GTTCCCAAAG GAATAGGTAA TAAGGATCAA CAAATTGGTT ATTGGAATAG ACAGATTCGT
6721 TATCGTATTG TAAAAGGCCA GCGTAAGGAA CTCGCTGAGA GGTGGTTCTT TTACTTCTTA
6781 GGTACAGGAC CTCATGCTGA TGCTAAATTC AAAGACAAGA TTGATGGAGT CTTCTGGGTT
6841 GCAAGGGATG GTGCCATGAA CAAGCCCACA ACGCTTGGCA CTCGTGGAAC CAATAACGAA
6901 TCCAAACCAC TGAGATTTGA TGGTAAGATA CCGCCACAGT TTCAGCTTGA AGTGAACCGT
6961 TCTAGGAACA ATTCAAGGTC TGGTTCTCAG TCTAGATCTG TTTCAAGAAA CAGATCTCAA
7021 TCTAGAGGAA GACACCATTC CAATAACCAG AATAATAATG TTGAGGATAC AATTGTAGCC
7081 GTGCTTGAAA AATTAGGTGT TACTGACAAA CAAAGGTCAC GTTCTAAACC TAGAGAACGT
7141 AGTGATTCCA AACCTAGGGA CACAACACCT AAGAATGCCA ACAAACACAC CTGGAAGAAA
7201 ACTGCAGGCA AGGGAGATGT GACAACTTTC TATGGTGCTA GAAGTAGTTC AGCTAACTTT
7261 GGTGATAGTG ATCTCGTTGC CAATGGTAAC GCTGCCAAAT GCTACCCTCA GATAGCTGAA
7321 TGTGTTCCAT CAGTGTCTAG CATAATCTTT GGCAGTCAAT GGTCTGCTGA AGAAGCTGGT
7381 GATCAAGTGA AAGTCACGCT CACTCACACC TACTACCTGC CAAAGGATGA TGCCAAAACT
7441 AGTCAATTCC TAGAACAGAT TGACGCTTAC AAGCGACCTT CTGAAGTGGC TAAGGATCAG
7501 AGGCAAAGAA GATCCCGTTC TAAGTCTGCT GATAAGAAGC CTGAGGAGTT GTCTGTAACT
7561 CTTGTGGAGG CATACACAGA TGTGTTTGAT GACACACAGG TTGAGATGAT TGATGAGGTT
7621 ACGAACTAAA CGCATGCCCG GGAATTCTGT GAGCGTATGG CAAACGAAGG AAAAATTAGT

```
7681 TATAGTAGCC GCACTCGATG GGACATTTCA ACGTAAACCG TTTAATAATA TTTTGAATCT
7741 TATTCCATTA TCTGAAATGG TGGTAAAACT AACTGCTGTG TGTATGAAAT GCTTTAAGGA
7801 GGCTTCCTTT TCTAAACGAT TGGGTGAGGA AACCGAGATA GAAATAATAG GAGGTAATGA
7861 TATGTATCAA TCGGTGTGTA GAAAGTGTTA CATCGACTCA TAATATTATA TTTTTTATCT
7921 AAAAAACTAA AAATAAACAT TGATTAAATT TTAATATAAT ACTTAAAAAT GGATGTTGTG
7981 TCGTTAGATA AACCGTTTAT GTATTTTGAG GAAATTGATA ATGAGTTAGA TTACGAACCA
8041 GAAAGTGCAA ATGAGGTCGC AAAAAAACTG CCGTATCAAG GACAGTTAAA ACTATTACTA
8101 GGAGAATTAT TTTTTCTTAG TAAGTTACAG CGACACGGTA TATTAGATGG TGCCACCGTA
8161 GTGTATATAG GATCTGCTCC CGGTACACAT ATACGTTATT TGAGAGATCA TTTCTATAAT
8221 TTAGGAGTGA TCATCAAATG GATGCTAATT GACGGCCGCC ATCATGATCC TATTTTAAAT
8281 GGATTGCGTG ATGTGACTCT AGTGACTCGG TTCGTTGATG AGGAATATCT ACGATCCATC
8341 AAAAAACAAC TGCATCCTTC TAAGATTATT TTAATTTCTG ATGTGAGATC CAAACGAGGA
8401 GGAAATGAAC CTAGTACGGC GGATTTACTA AGTAATTACG CTCTACAAAA TGTCATGATT
8461 AGTATTTTAA ACCCCGTGGC GTCTAGTCTT AAATGGAGAT GCCCGTTTCC AGATCAATGG
8521 ATCAAGGACT TTTATATCCC ACACGGTAAT AAAATGTTAC AACCTTTTGC TCCTTCATAT
8581 TCAGGGCCGT CGTTTTACAA CGTCGTGACT GGGAAAACCC TGGCGTTACC CAACTTAATC
8641 GCCTTGCAGC ACATCCCCCT TTCGCCAGCT GGCGTAATAG CGAAGAGGCC CGCACCGATC
8701 GCCCTTCCCA ACAGTTGCGC AGCCTGAATG GCGAATGGCG CCTGATGCGG TATTTTCTCT
8761 TTACGCATCT GTGCGGTATT TCACACCGCA TATGGTGCAC TCTCAGTACC ATCTGCTCTG
8821 ATGCCGCATA GTTAAGCCAG TACACTCCGC TATCGCTACG TGACTGGGTC ATGGCTGCGC
8881 CCCGACACCC GCCAACACCC GCTGACGCGC CCTGACGGGC TTGTCTGCTC CCGGCATCCG
8941 CTTACAGACA AGCTGTGACC GTCTCCGGGA GCTGCATGTG TCAGAGGTTT TCACCGTCAT
9001 CACCGAAACG CGCGAGGCAG
```

RECOMBINANT RACCOON POX VIRUSES AND THEIR USE AS AN EFFECTIVE VACCINE AGAINST FELINE INFECTIOUS PERITONITIS VIRUS DISEASE

This is a division of application Ser. No. 08/125,516, filed Sep. 22, 1993, now abandoned.

FIELD OF THE INVENTION

The present invention pertains to the prophylaxis of disease caused by feline infectious peritonitis virus (FIPV), using recombinant raccoon pox viruses (RRPVs) expressing the nucleocapsid and transmembrane proteins of FIPV as vaccines.

BACKGROUND OF THE INVENTION

Feline infectious peritonitis virus (FIPV) induces a systemic infection in cats that is often fatal. The effusive form of the disease is characterized by accumulation of fibrinous ascitic fluid. The non-effusive form of the disease is characterized by granulomatous lesions in multiple organs including, but not limited to, liver, spleen, kidneys, lung, and intestines. Reviewed in Barlough, J. E. and C. A. Stoddart. Feline Coronaviral Infections in C. E. Greene (Ed.). *Infectious Diseases of the Dog and Cats.* W. B. Saunders Co., Philadelphia, Pa., 1990, pp. 300–312.

Feline infectious peritonitis virus is a coronavirus composed of three major structural proteins: The S (spike) protein, the E1 or M (transmembrane) protein, and the N (nucleocapsid) protein. Venema et al., Virology 181: 327–335, 1991 and Dale, et al., EPO 0,376, 744.

Prior vaccines intended to prevent FIPV infection have actually been shown to exacerbate the disease caused by this virus. Pedersen, N. C. and J. W. Black, Am. J. Vet. Res. 44: 229–234, 1983; Vennema H., et al., J. Virol. 64: 1407–1409, 1990; Barlough, J. E., Can. J. Comp. Med. 49: 303–307, 1985; Barlough J. E. et al., Lab. Anim. Sci. 34: 592–597, 1984; Stoddart, C. A., et al., Res. Vet. Sci. 45: 383–388, 1988; and Pedersen, N. C., Adv. Vet. Sci. Comp. Med. 33: 413–428, 1989. This phenomenon apparently reflects an immune enhancement of infection mediated by immunoglobulins produced in response to the virus, in particular by those antibodies directed against the S protein. Olsen C. W. et al., J. Virol. 4: 175–189, 1981. Therefore, the best candidate vaccine for prophylaxis of this disease would be a preparation that induces strong cell-mediated immunity in the absence of enhancing antibodies. This could be accomplished with a vaccine that lacks the outer envelope protein but contains the other structural proteins of FIPV (N and E1). Prior attempts to vaccinate cats with a recombinant vaccinia virus expressing the N or E1 proteins of FIPV, however, have failed to induce strong protective immunity. Venema et al., Virology 181:327–335, 1991 and Dale, et al., European Patent Application 0,376,744. See also, Venema, European Patent Application 0,411,684.

What is needed in the art, therefore, is an effective vaccine against FIPV that utilizes the N and E1 proteins, or segments therefrom, as immunogens.

SUMMARY OF THE INVENTION

The present invention pertains to the induction of protective immunity to FIPV in cats. One object of the invention is to provide recombinant raccoon poxviruses containing the genes for the FIPV N or M/E1 proteins (RRPV-N and RRPV-E1, respectively).

A further object of the invention is to provide a feline vaccine comprising RRPV-N or RRPV-E1, either singly or in combination, or in combination with other viruses, bacteria, or fungi that have been inactivated or attenuated.

A still further object of the invention is to provide a method for preventing disease caused by FIPV, by administering to a feline in need of such treatment a vaccine comprising RRPV-N, RRPV-E1, or combinations thereof.

These and other objects and advantages, which will be apparent from this specification, are achieved by the invention described below.

DESCRIPTION OF THE DRAWINGS

FIGS. 1A through 1E, when joined at respective match lines A—A through D—D, illustrate the nucleotide and amino acid sequence of the FIPV E1 protein (SEQ ID NO:1 and SEQ ID NO:5, respectively.

FIGS. 2A through 2G, when joined at respective match lines A—A through F—F, illustrate the nucleotide and amino acid sequence of the FIPV N protein (SEQ ID NO:2 and SEQ ID NO:6, respectively).

FIGS. 5A to 5F, when joined at respective match lines A—A through E—E, illustrate the nucleotide sequence of pSC11 E1.

FIGS. 6A through 6F, when joined at respective match lines A—A though E—E, illustrate the nucleotide sequence of pSC11 FIPV N.

DETAILED DESCRIPTION OF THE INVENTION

Figure 3A:
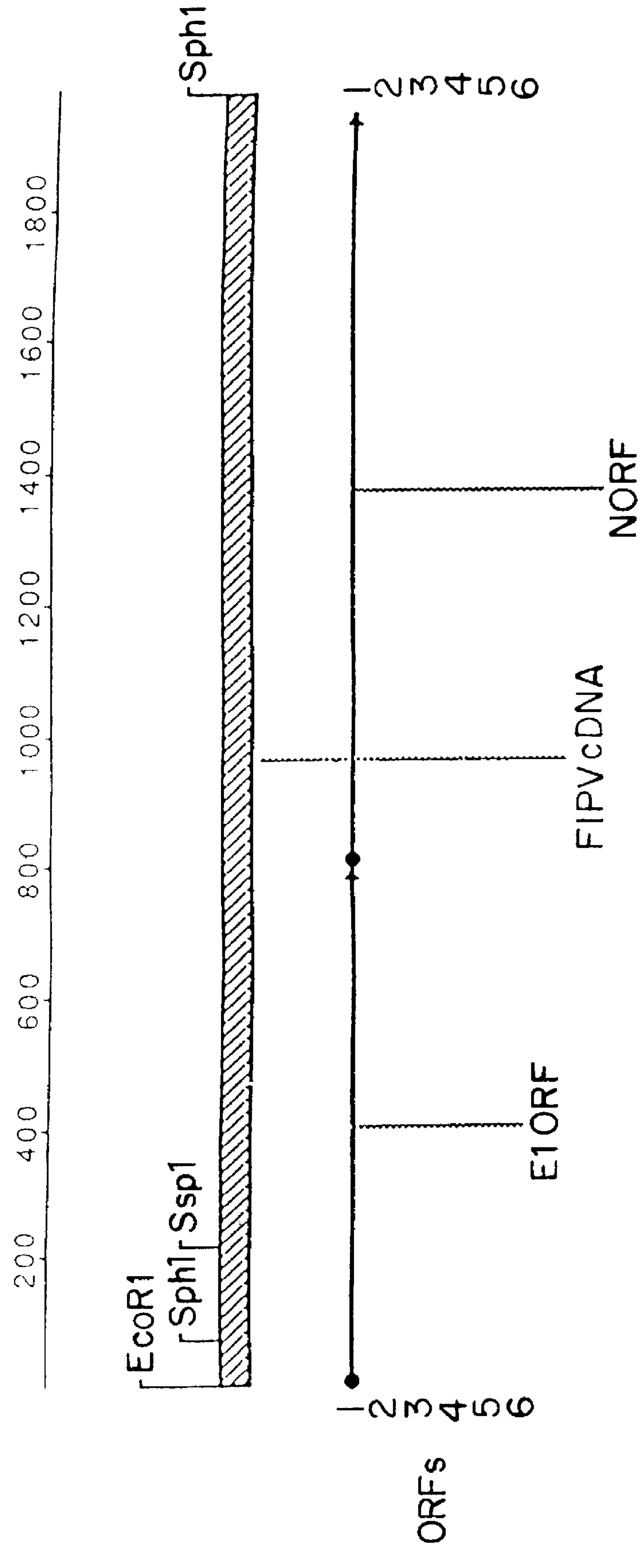
FIGS. 3A and 3B illustrate the plasmid used to clone the genes encoding the FIPV E1 and N proteins.

The vaccine of the present invention may be prepared by creating recombinant raccoon poxviruses (RRPVs) containing the genes encoding the N or E1 proteins of FIPV or immunogenic fragments thereof. These genes are first inserted into a transfer plasmid, which is then introduced into appropriate host cells that have been previously infected with a raccoon poxvirus. As a result, the DNA from the transfer plasmid is incorporated into the poxvirus DNA by homologous recombination, producing the RRPVs that are released from the cells.

DNA encoding the FIPV N or E1 proteins is inserted into the transfer plasmid immediately downstream of a poxvirus promoter. In a preferred embodiment, the early/late 7.5 Kd protein promoter of vaccinia virus is used; however, alternate promoter elements that are functional in poxviruses can also be used.

The preferred transfer plasmid also contains a beta-galactosidase marker gene, which allows for selection and detection of the plasmid DNA sequences in recombinant viruses. It will be obvious to one skilled in the art that alternative selectable marker genes, such as the neomycin resistance gene or the *E. coli* gpt gene or others, can be used to practice the invention. Flanking the foreign gene of interest and the selectable marker gene are thymidine kinase DNA sequences, which facilitate recombinatorial integration of the plasmid DNA sequences into the raccoon poxvirus DNA.

Recombinant viruses expressing the FIPV N or E1 genes are prepared by first infecting a susceptible cell line such as Vero (ATCC CCL 81), BSC-1 (ATCC CCL 26), RAT-2 (ATCC CRL 1764), or CRFK (ATCC CCL 941) with wild type raccoon poxvirus (ATCC VR-838 or similar isolates, such as, for example, RCNV71-I-85A). Transfer plasmid DNA containing the E1 or N gene is then transfected into the infected cells using cationic liposome-mediated transfection, or other suitable techniques such as electroporation or calcium phosphate precipitation. Virus replication is allowed to proceed until cytopathic effects are noted in all cells.

Incorporation of the FIPV E1 or N genes into poxvirus DNA is accompanied by disruption of the viral thymidine kinase gene. Therefore, virus harvested from this infection may be isolated by selecting for the absence of a thymidine kinase gene; this is achieved by growth on tk- RAT-2 cells (ATCC CRL 1764) in the presence of 5-bromodeoxyuridine. Viruses containing a gene insert from the transfer plasmid are further identified by the appearance of a blue plaque color when grown in the presence of a chromogenic substrate for beta-galactosidase such as X-gal.

Viral plaques that survive these selection and screening procedures are then subjected to several cycles of plaque purification. Subsequently, the presence of the E1 or N genes is confirmed by polymerase chain reaction technology, and the presence of E1 or N protein is confirmed by immunoblot analysis using specific antibodies. These viruses are designated RRPV-FIPV E1 and RRPV-FIPV N, respectively.

In a further embodiment of the present invention, the genes encoding N and E1 were inserted into a single transfer plasmid. Introduction of this plasmid into cells previously infected with wild-type raccoon poxvirus results in the production of recombinant viruses that express both proteins simultaneously (RRPV-FIPV E1/N).

In a still further embodiment, RRPVs can be produced that express less-than-full-length segments of the FIPV E and N proteins. The techniques used to engineer transfer plasmids encoding partial sequences of E1 and N are well-known and widely used in the art, as are the methods for production and screening of RRPVs as detailed in this specification. For example, introduction of oligonucleotides containing a stop codon at various points along E1 or N DNA will produce a nested set of carboyxterminal-truncated versions of that gene, which can then be incorporated into RRPVs. It will be apparent to one of ordinary skill in the art that systematic screening of such recombinant RRPVs can establish whether the intact protein, or subfragments thereof, are most preferred in practicing the present invention. Furthermore, as stated above, DNA encoding different fragments of E1 and N can be used in a combination vaccine after incorporation into the same, or different, RRPVs.

For vaccine preparation, susceptible cells such as those listed above are infected with RRPVs at a multiplicity of infection (MOI) of 0.1 infectious units/cell or less. In this specification, an infectious unit is defined as a Tissue Culture Infectious Dose ($TCID_{30}$), an amount of virus yielding 50% infection under defined conditions. A method for $TCID_{50}$ determination is detailed in Example 1 below. When cytopathology is noted in >90% of the cells, the infected cells and extracellular fluids (both of which contain viruses) are harvested as a single virus-cell lysate.

The highly concentrated virus stock to be used as a vaccine may be stored frozen (−50° C. or colder) or lyophilized until the time of use. Compounds such as NZ-amine, dextrose, gelatin or others designed to stabilize the virus during freezing and lyophilization may be added. The virus initially present in the virus-cell lysate may be further concentrated using commercially available equipment.

Typically, the concentration of virus in the vaccine formulation will be a minimum of $10^{6.5}$ $TCID_{50}$ per dose, but will typically be in the range of $10^{7.0}$ to $10^{9.0}$ $TCID_{50}$ per dose. At the time of vaccination, the virus is thawed (if frozen) or, if lyophilized, is reconstituted with a physiologically-acceptable carrier such as deionized water, saline, phosphate buffered saline, or the like.

The present invention is not limited to native (i.e. replication-competent) RRPVs. The virus-cell lysate can be subjected to treatments commonly used in the art to inactivate viruses. A composition comprising inactivated virus and expressed protein will be effective in eliciting protective immunity against FIPV if it contains a sufficient quantity of FIPV protein. This type of vaccine would provide added assurance that recipient felines will not be exposed to infectious FIPV as a consequence of vaccination. In addition, a physiologically-acceptable adjuvant may be added to the virus, such as EMA 31 (Monsanto Co., St. Louis, Mo.), NEOCRYL (Polyvinyl Chemical Industries, Wilmington, Mass.), MVP (Modern Veterinary Products, Omaha, Nebr.), Squalene, Pluronic L121, or the like.

Individual raccoon poxviruses expressing the N or E1 genes may be mixed together for vaccination. Furthermore, the virus may be mixed with additional inactivated or attenuated viruses, bacteria, or fungi such as feline leukemia virus, feline panleukopenia virus, feline rhinotracheitis virus, feline calicivirus, feline immunodeficiency virus, feline herpesvirus, feline enteric coronavirus, feline *Chlamydia psittaci, Microsporum canis*, or others. In addition, antigens from the above-cited organisms may be incorporated into combination vaccines. These antigens may be purified from natural sources or from recombinant expression systems, or may comprise individual subunits of the antigen or synthetic peptides derived therefrom.

In a further embodiment of the present invention, live or inactivated RRPV virus-cell lysates can be incorporated into liposomes, or encapsulated in peptide-, protein-, or polysaccharide-based microcapsules prior to administration, using means that are known in the art.

The final vaccine is administered to cats in a volume that may range from about 0.5 to about 5 ml. The vaccine can be administered by subcutaneous, intramuscular, oral intradermal, or intranasal routes. The number of injections and their temporal spacing may be varied. One to three vaccinations administered at intervals of one to three weeks are usually effective.

The following examples are intended to further illustrate the invention without limiting its scope. The techniques used to infect and transfect cells, plaque purify virus, perform immunoblot analysis are widely practiced in the art.

EXAMPLE 1

Figure 3B:
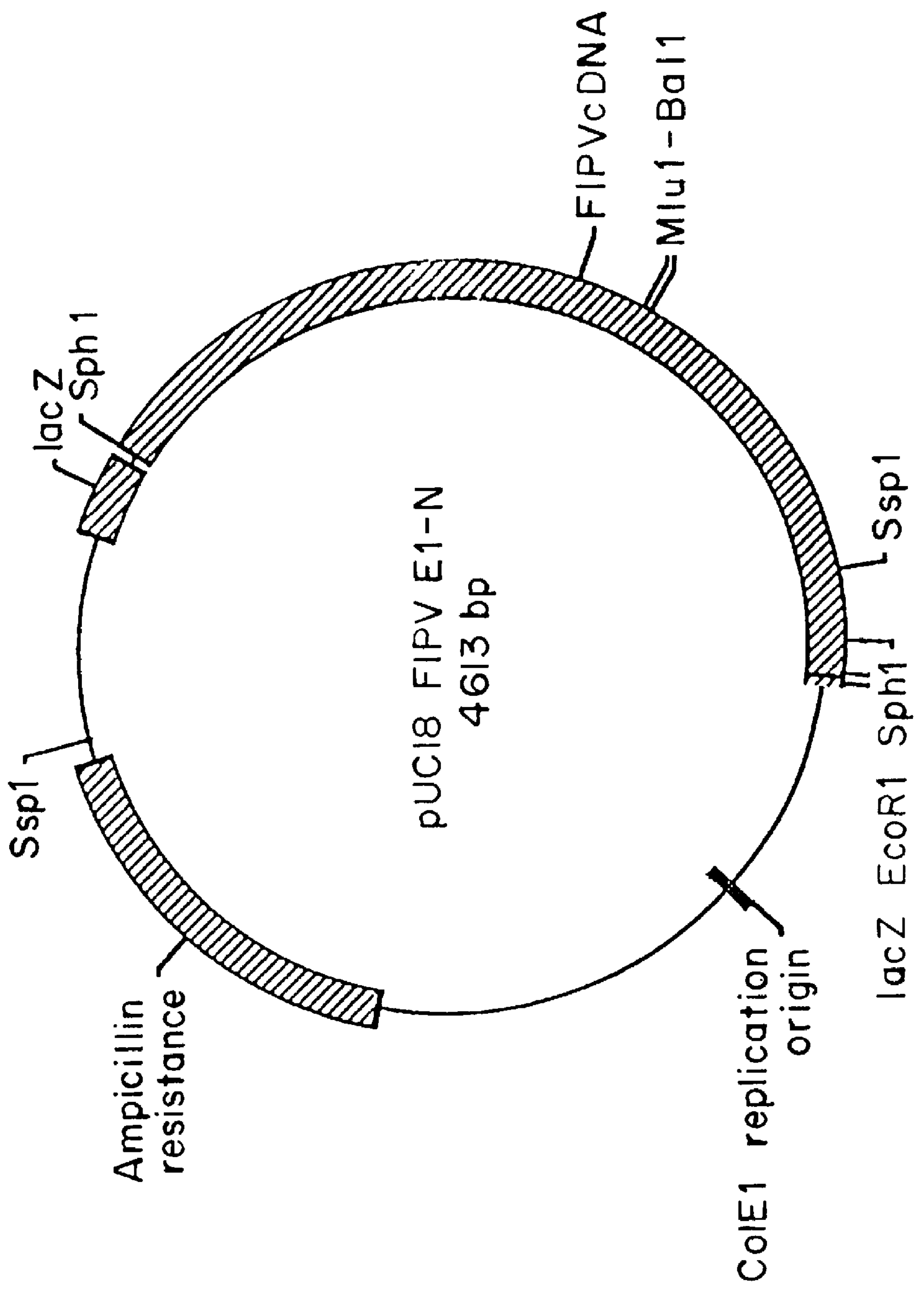
Figure 4A:
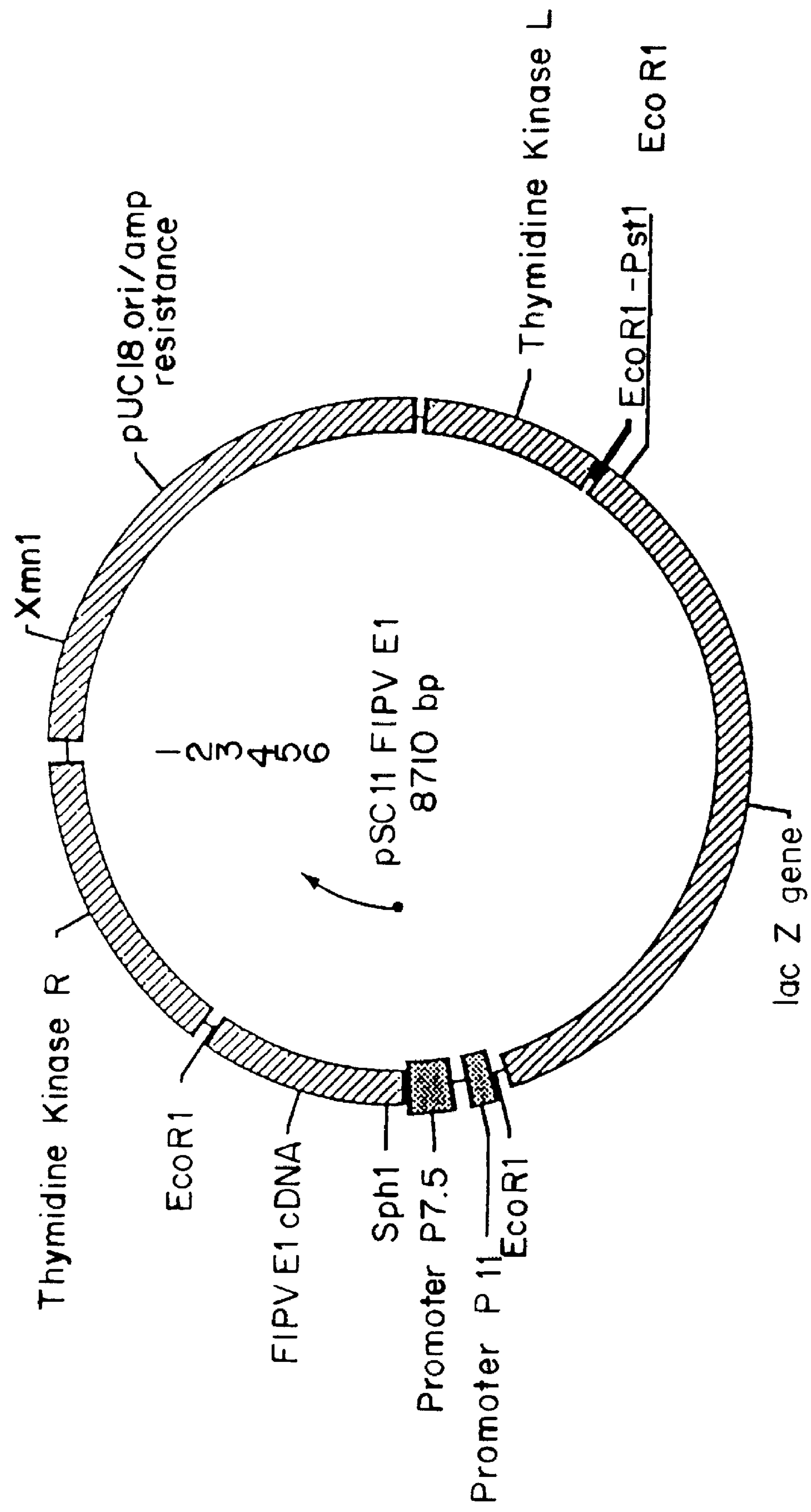
FIG. 4A schematically shows the pSC11 transfer plasmid used to create RRPVs encoding the E1 protein.
Figure 4B:
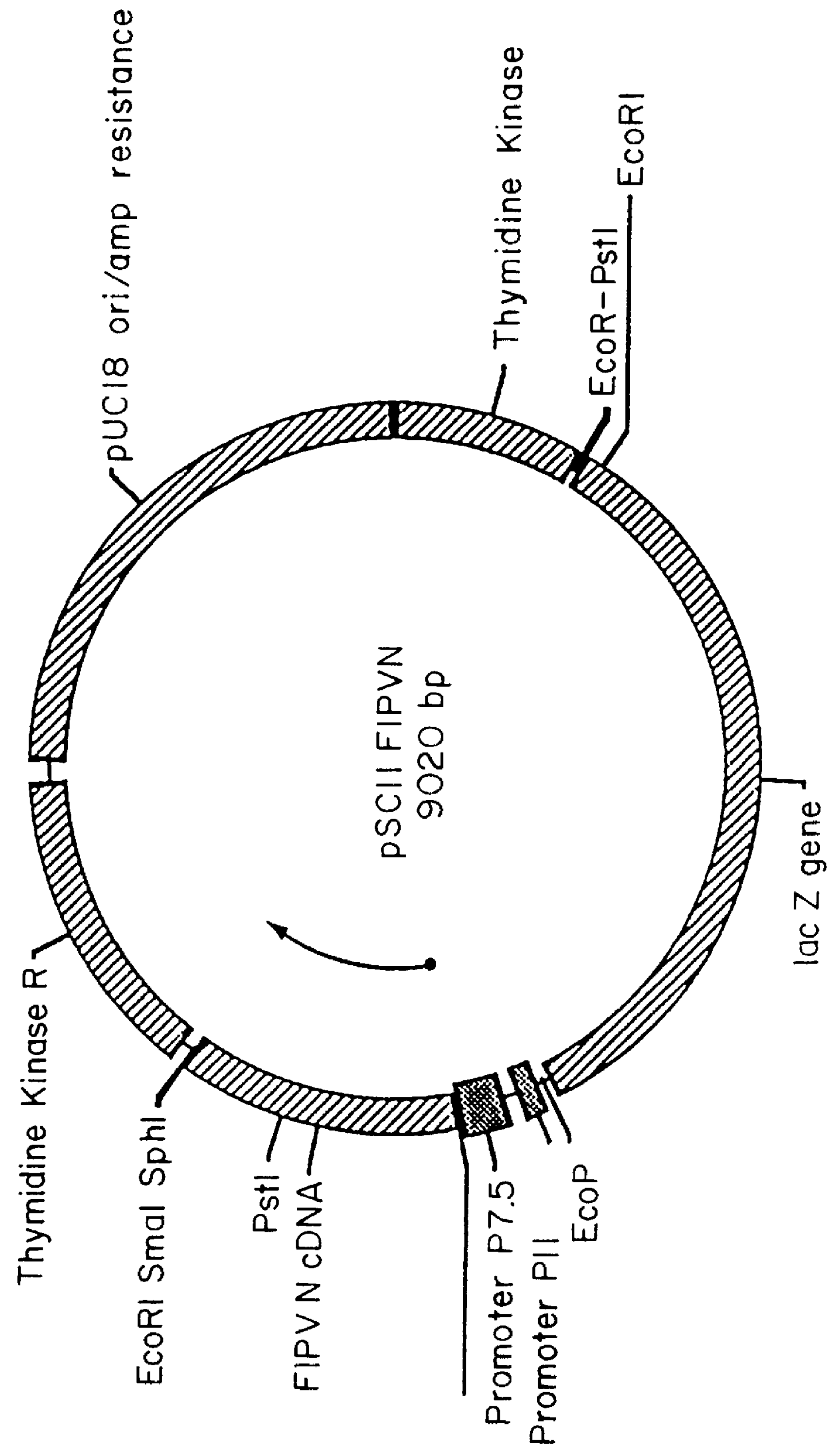
FIG. 4B schematically shows the pSC11 transfer plasmid used to create RRPVs encoding the N protein.

Generation of Recombinant Raccoon Pox Viruses Expressing FIPV N and E1 Genes 1. Cloning of FIPV N and E1 Genes and Preparation of Transfer Plasmids The sequences of the E1 SEQ. ID. NO:1 and N SEQ. ID. NO:2 genes used in the present invention are shown in FIGS. 1A to 1E and 2A to 2G, respectively, of the specification. The methods for cloning of the N and E1 genes of FIPV and their insertion into a pSC11 transfer vector are detailed in European Patent Application 0,376,744, which is incorporated by reference. The plasmid used to clone the cDNA for the E1 and N genes is shown in FIGS. 3A and 3B. The pSC11 plasmids carrying the E1 and N genes are shown in FIGS. 4A and 4B, respectively. The sequences of these plasmids are shown in FIGS. 5A to 5F (SEQ ID NO:3) and FIGS. 6A to 6F (SEQ ID NO:4).

To construct a pSC11 transfer plasmid containing both N and E1 genes, a 1.0 kb DNA fragment containing the vaccinia 7.5 promoter and the E1 gene was inserted downstream of the N gene in pSC11-FIPV N. The resulting plasmid was designated pSC11-FIPV N/E1.

2. Preparation of Recombinant Raccoon Poxviruses (RRPVs)

Monolayers of Vero cells (ATCC CCL 81) that were 80% confluent (approximately $5\times10^6$ cells/100 mm tissue culture dish) were infected for 30–60 minutes at 37° C. with wild-type raccoon pox virus (ATCC VR-338) at a multiplicity of infection (MOI) of 0.1 $TCID_{50}$/cell. The medium (2 ml) consisted of Eagle's Minimum Essential Medium ("MEM", Gibco BRL #410-1500) containing 0.05% lactalbumin hydrolysate and 15 $\mu$g/ml gentamicin sulfate and adjusted to pH 7.2 with sodium bicarbonate. After infection, the medium was removed and the cells were transfected with the pSC11-FIPV N, pSC11-FIPV E1, or pSC11 N/E1 transfer plasmid by cationic liposome-mediated transfection using Transfectam@ (Promega Corporation, Madison, Wis.) and DOTAP (Boehringer Mannheim, Indianapolis, Ind.), respectively, per manufacturer's instructions. The cells were incubated with the DNA-liposomes mixture in 3 ml of MEM containing 5% fetal bovine serum (FBS) overnight at 37° C. (5% $CO_2$), after which the medium was replaced with 8 ml of fresh MEM-5% FBS. The transfected cells were incubated at 37° C. (5% $CO_2$) until greater than 80% showed cytopathic effects (CPE), which took approximately 3–4 days. The virus-cell lysates were then removed from the plates and subjected to two cycles of freeze-thawing before storage at −70° C.

3. Isolation of Recombinant Raccoon Pox Virus Carrying the FIPV N Gene

RRPVs carrying the FIPV N gene (RRPV-FIPV N) were isolated and purified from the pSC11-FIPV N- Vero cell transfection by standard viral plaque purification methods. Monolayers of Vero cells (50–80% confluent) were infected with 2 ml of ten-fold serial dilutions ($10^{-1}$ to $10^{-3}$) of the viral-cell lysates for 1 hour at 37° C. After incubation, the media was removed and the infected cells were overlaid with 8–10 ml of 1.25% Noble agar containing MEM/5% FBS. The infected cells were then incubated for 3–4 days at 37° C. (5% $CO_2$), and overlaid again with 4 ml of 1.25% Nobel agar containing 0.5X PBS and 600 $\mu$g/ml 5-bromo-4-chloro-3-indolyl-β-D-galactopyranoside (X-gal, States Biochemical Cleveland, Ohio). The plates were incubated at 37° C. (5% $CO_2$) for 4–16 hours, until blue (i.e. β-galactosidase positive) viral plaques were observed. The recombinant viral plaques were picked with sterile blunt needles attached to a 1 cc syringe, suspended in 0.5 ml of 0.25 $\mu$g/ml trypsin, vortexed vigorously, and incubated at 37° C. for 15–30 min. The disrupted viral plaques were then inoculated onto $5\times10^5$ Vero cells in 25 $cm^2$ flasks and incubated at 37° C. (5% $CO_2$) until greater than 80% CPE was observed. The viral-cell lysates containing RRPV-FIPV N were subjected to two cycles of freeze-thawing and stored at −70° C. Six individual RRPV-FIPV N clones were selected and plaque-purified five times as described above.

4. Isolation of Recombinant Raccoon Pox Virus Containing the FIPV E1 Gene

RRPVs carrying the FIPV E1 gene (RRPV-FIPV E1) were isolated and purified from pSC11-FIPV E1-transfected Vero cells using the methods described for rRPV-FIPV N, with some modifications. In this case, thymidine kinase deficient (tk-) RRPVs from the initial virus-cell lysates were selected on tk- RAT-2 cells (ATCC CRL 1764). This was performed by inoculating 1 ml of the initial virus-cell lysate onto a monolayer of RAT-2 cells in a 75 $cm^2$ flask (approximately $5\times10^6$ cells) in the presence of 5-bromodeoxyuridine (BrdU) at 30 $\mu$g/ml in MEM. The infected monolayer was incubated at 37° C. (5% $CO_2$) for 3–4 days until greater than 70% CPE was observed. The tk- virus-cell lysates were subjected to two cycles of freeze-thawing before storage at −70° C. Two individual RRPV-FIPV E1 clones were selected and subjected to six cycles of plaque purification as described above for RRPV-FIPV N.

5. Confirmation of FIPV N and E1 Genes in RRPV by Polymerase Chain Reaction

The presence of the FIPV N and E1 genes in the RRPVs was confirmed using the polymerase chain reaction (PCR). 90 $\mu$l of a virus-cell lysate were incubated with 10 $\mu$l of tenfold concentrated PCR lysis buffer (100 mM Tris-HCL buffer, pH 8.5; 500 mM KCl; 25 MM $MgCl_2$: 5% Tween 20; 3 mg/ml Proteinase K) for 16 hours at 50° C., then boiled for 10 min. 10 $\mu$l of this lysate was used in the PCR. PCR was performed in 100 $\mu$l of 10 mM Tris-HCL buffer, pH 8.3; 50 mM KCl; 200 uM of each deoxyribonucleotide triphosphate, 1.5 mM $MgCl_2$: 30 pmoles of each oligonucleotide primer; and 2.5 units of AmpliTaq@ DNA polymerase (Perkin-Elmer Cetus, Norwalk, Conn.). The primers used in the PCR for FIPV N were:

5'-CTCGTGGTCGGAAGAATAATGATA-3' SEQ. ID. NO:7 (1)

5'-AGCACCATAGAAAGTTGTCACATC-3' SEQ. ID. NO:8, (2)

corresponding to nucleotides 68–91 and 721–744 of the FIPV N open reading frame (primers 1 and 2, respectively). The primers used in the PCR for FIPV E1 were:

5'-TATGTAATGTTCGGCTTTAGTG-3' SEQ. ID. NO:9 (3)

5'-GTGCTTCTGTTGAGTAATCACC-3' SEQ. ID. NO:10 (4)

corresponding to nucleotides 334–355 and 721–742 of the FIPV E1 open reading frame (primers 3 and 4, respectively). The PCR amplifications were performed in a DNA Thermal Cycler (Perkin-Elmer Cetus) by first heating the reaction mixes to 94° C. for denaturation, and then performing 35 cycles of amplification, each consisting of 1 min at 95° C., 1 min at 55° C., 2 min at 72° C., and, on the last cycle, a final incubation of 8 min at 72° C. 10 $\mu$l of the PCR products were resolved by electrophoresis in a horizontal-submarine 4% NuSieve agarose gel (FMC BioProducts, Rockland, Me.) in TAE buffer (40 mM Tris base, 20 mM sodium acetate, 1 mM EDTA, pH 7.2) by applying 5 V/cm for 1–2 hours. The DNA products were visualized by staining the gels with ethidium bromide.

Figure 7:
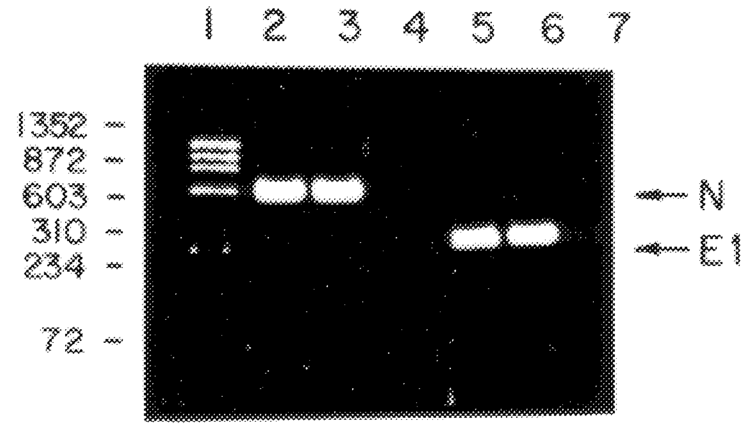
FIG. 7 is a photograph of an ethidium bromide-stained agarose gel showing the analysis of RRPV-FIPV N and RRPV-FIPV E1 by polymerase chain reaction.

PCR amplifications with the FIPV N and E1 primers gave DNA fragments of 676 and 408 nucleotides, respectively (FIG. 7). PCR amplifications using the pSC11 FIPV N and E1 transfer plasmids served as positive controls, and showed products of the predicted sizes. PCR amplifications using wild-type raccoon pox virus-Vero cell lysates served as a negative control, and no PCR products were observed in those samples.

6. Confirmation of RRPV FIPV N and E1 Protein Expression by Immunoblot Analysis

Confluent monolayers of Vero cells in a 25 $cm^2$ flask (1–2×$10^6$ cells) were infected with clones of either RRPV-FIPV N or RRPV-FIPV E1 at an MOI of 0.1. The infected cells were incubated at 37° C. (5% $CO_2$) for 2–3 days until approximately 80% of the cells showed cytopathic effects. A virus-cell lysate was prepared, and 20 $\mu$l of the sample were added to 5 $\mu$l of 5X Laemmli sample buffer (0.3M Tris-HCI buffer, pH 6.8, containing 5% SDS, 50% glycerol, 0.4% bromophenol blue, and 3% 2-β-mercaptoethanol) and heated at 95° C. for 5 min. The denatured protein samples were separated by SDS/polyacrylamide electrophoresis using a 4-15% gradient polyacrylamide gel as described previously. Maniatis et al., Molecular Cloning: A Laboratory Manual, 1982, Cold Spring Harbor Press. After electrophoresis, the proteins were transferred to nitrocellulose (Bio-Rad Laboratories, Hercules, Calif.) by electrotransfer using a Bio-Rad transfer apparatus per manufacturer's instructions. The transfer was performed in 25 mM Tris-HCI buffer, containing 0.2M glycine and 20% methanol, for 45 minutes at 50V with constant current.

Figure 8:
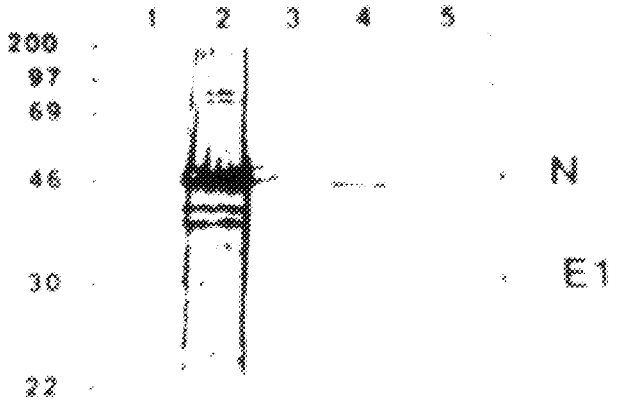
FIG. 8 is an immunoblot illustrating the detection of FIPV N and E1 proteins in virally infected cell lysates.

FIPV N and E1 proteins were visualized on the nitrocellulose filter using specific antibodies. Davis et al., Basic Methods in Molecular Biology, 1986, Elsevier Science Publishing Company, New York, N.Y. The filter was rinsed in phosphate buffered saline pH 7.4 containing 0.1% Tween-20 ("PBS-TW"), after which non-specific sites were blocked by overnight incubation at 4° C. in PBS containing 1% bovine serum albumin (PBS-BSA) followed by a 15 min wash in PBS-TW. The filter was then incubated for 30 min at room temperature with anti-FIPV antibodies, which consisted of ascites fluid from a FIPV (strain 79-1146)-infected cat, diluted 1:100 in PBS-TW containing 1% BSA ("PBS-TW-BSA"). After four 5 min washes in PBS-TW, the filter was incubated for 30 min at room temperature with a secondary antibody consisting of biotin-labeled mouseanti-cat IgG antibody (Kirkegaard & Perry Laboratories Inc., Gaithersburg, Md.) that had been diluted 1:2000 in PBS-TW-BSA, followed by four 5 min washes in PBS-TW. The filter was then incubated for 30 min at room temperature with horseradish peroxidase-conjugated streptavidin (Kirkegaard & Perry Laboratories Inc.) that had been diluted 1:1000 in PBS-TW. After the filter was washed four times (5 min each) in PBS-TW, the antigen-antibody complexes were visualized with peroxidase chromogenic substrate (Kirkegaard & Perry Laboratories Inc.). Sucrose-gradient purified FIPV and wild-type raccoon pox virus-Vero cell lysates were used as the positive and negative controls, respectively. A typical immunoblot is shown in FIG. 8.

7. Raccoon Poxvirus Titration

Serial tenfold dilutions of virus are prepared in MEM and inoculated in replicates of five onto Vero cells (1×$10^4$ cells per well) in a $96^-$ well plate. Virus preparations may be pretreated by dilution into an equal volume of 0.5% trypsin and incubation at 37° C. for 30 min in order to release virus from inclusions. Plates are incubated for 3–5 days at 37° C. (5% $CO_2$) and observed for cytopathology typical of raccoon poxvirus. Titers are calculated as 50% endpoints based on cytopathology using the methods of Reed and Muench, *The American Journal of Hygiene* 27(3):493–497) (1938).

EXAMPLE 2

Preparation of Vaccine and Testing for Efficacy in Cats

1. Preparation of Master Seeds of RRPV-FIPV N and E1 Viruses

A single clone of each recombinant virus was selected for large-scale expansion to serve as a master seed virus. The criteria for selection were: 1) Demonstration of purity. Polymerase chain reaction was utilized to insure that the clone was uncontaminated with wild type virus. 2) Demonstration of adequate recombinant proten expression by Western blot or other antigen detection methods.

All recombinant virus expansions and titrations were done on Vero cells in MEM containing 2.5% FBS. Each plaque purified virus clone was expanded by inoculating a confluent monolayer of Vero cells in a 150 $cm^2$ flask (1×$10^7$ cells) with 1 ml of viral-cell lysate (approximately $10^7$ infectious virus particles), and incubating at 37° C. (5% $CO_2$) until 100% cytopathic effect was observed (2–3 days). This virus-cell lysate was titrated on Vero cells as described in Example 1, and served as a premaster seed virus stock to obtain the master seed virus. The MOI to be used to produce the highest titer master seed virus was determined by inoculating a confluent monolayer of Vero cells in a roller bottle (1×$10^8$ cells) with various MOIs of recombinant virus (e.g. 0.1, 0.05, 0.01, 0.005, and 0.001 $TCID_{50}$/cell.) The infected cells were incubated at 37° C. until greater than 80% CPE was observed (approximately 3 days), and the titers of each infected roller bottle was determined. The master seed viruses were aliquoted into 1.5 ml ampules, which were sealed and stored in a liquid nitrogen freezer.

2. Preparation of Vaccines

3×$10^7$ Vero cells were seeded into 850 $cm^2$ roller bottles in 200 ml of growth media (MEM containing 0.5% lactalbumin hydrolysate and 5% FBS) and incubated for 18 hours at 37° C. The next day, the medium was removed from the cells and replaced with 50 ml of RRPV-FIPV N virus diluted to an MOI of 0.01 in infection media (MEM containing 0.5% lactalbumin hydrolysate and 2.5% FBS). The virus used was at the second passage beyond the master seed preparation. Virus was allowed to absorb to the cells for 30 min at 37° C., after which the volume of medium was adjusted to 150 ml per roller bottle. Roller bottles were incubated at 37° C. until 100% cytopathology was evident (3 days). The virus-cell lysate was harvested and stored frozen (−70° C.). The virus titer was determined to be $10^{6.97}$ $TCID_{50}$/ml.

RRPV-FIPV E1 stocks were prepared in the same manner, except that an MOI of 0.1 was used. The final virus preparation was titered and found to contain $10^{6.5}$ $TCID_{50}$/ml. Wild type raccoon poxvirus was grown using the same methods as described above, and contained $10^{6.44}$ $TCID_{50}$/ml.

3. Vaccination

A group of twenty-four 9-month-old cats (specific pathogen-free, Harlan Sprague Dawley, Madison, Wis.), comprising seven males and seventeen females, was used to demonstrate the efficacy of the RRPV-FIPV N vaccine. Cats were divided into five groups and vaccinated twice, 21 days apart, as indicated below:

| Group | # Cats | Vaccine | Volume (ml) | Viral Dose ($TCID_{50}$) | Vaccination Route* |
|---|---|---|---|---|---|
| 1 | 5 | RRPV-FIPV N | 3 | $10^{7.44}$ | SC |
| 2 | 5 | RRPV-FIPV N | 1 | $10^{6.97}$ | IM |
| 3 | 5 | RRPV-FIPV N | 3 | $10^{7.44}$ | ORAL |
| 4 | 4 | RRPV-FIPV N (1:10 Dilution) | 3 | $10^{6.44}$ | SC |
| 5 | 5 | Wild Type RPV | 3 | $10^{6.44}$ | SC |

*SC = Subcutaneous
IM = Intramuscular
Oral = Oral

4. Challenge

Two weeks following the second vaccination, cats were orally inoculated with $10^{3.4}$ $TCID_{50}$ of Feline Enteric Coronavirus (strain 79-1683, ATCC VR-989). This virus induces a subclinical infection which can enhance subsequent FIPV infection. Three weeks later, cats were orally challenged with $10^{3.4}$ $TCID_{50}$ of FIPV (strain 79-1146, ATCC VR-990). Cats were monitored weekly for a total of 64 days after challenge for signs of clinical disease including: fever, icterus, leukopenia, anemia, weight loss, anorexia, depression, dehydration, and peritoneal swelling. Cats deemed moribund were euthanized by the attending veterinarian and post-mortem pathological examination was performed. Clinical disease signs were scored as follows:

| SIGN | | SCORE |
|---|---|---|
| Fever | 103.0–103.9° F. | 1 point/day* |
| | 104.0–104.9° F. | 2 points/day |
| | ≧105.0° F. | 3 points/day |
| Dehydration | | 1 point/day |
| Depression | | 1 point/day |
| Anorexia | | 1 point/day |
| Peritoneal Swelling | | 1 point/day |
| Icterus | | 1 point/day |
| Weight Loss | >20% | 1 point per observation |
| | >30% | 2 points per observation |
| | >50% | 5 points per observation |
| Leukopenia | decrease of 50% | 3 points per observation |
| | counts <6000 | 2 points per observation |
| Hematocrit | <25% PCV | 3 points per observation |
| Death | | 25 points |

*For cats with baseline temperatures averaging 103° F., no points will be scored until temperatures are in excess of 1° F. above baseline.

5. Evaluation of Induced Immunity to FIPV

Inoculation with virulent FIPV induced a fatal infection in 4/5 (80%) of the control cats, which were vaccinated with wild type raccoon poxvirus (Table 1). Both effusive and non-effusive forms of the disease were noted in the control cats. On the other hand, clinical disease was essentially absent after challenge of the subcutaneous vaccinates. The sporadic fever in these cats could be attributed to excitability and the slight anemia on one day in cat 1264 is not a significant finding. The subcutaneous vaccinates showed a statistically significant reduction in clinical signs ($p<0.05$, by ANOVA) and death ($p<0.01$, by Chi Square Analysis) when compared to the control cats.

The intramuscular route of vaccination was less effective in that 2/5 (40%) of the cats succumbed to FIPV-induced disease. However, the onset of disease in these cats was delayed when compared to the controls. The decreased efficacy may be related to the lower titer of virus inoculated into these cats because only a 1 ml dose could be administered by this route. There was also decreased efficacy when cats were inoculated by the oral route (60% mortality) which may indicate the need for a higher virus dose when vaccinated by this route.

The protection conferred against FIPV-caused disease by the subcutaneously administered vaccine was shown to be dose-dependent, confirming the benefit of a high-titer RRPV-FIPV vaccine in inducing protection against clinical disease induced by FIPV virus. A suitable vaccine dose contains viral antigen in the range of $10^4$–$10^8$ $TCID_{50}$/ml, preferably $10^7$–$10^8$ $TCID_{50}$/ml. A typical dose for administration to cats is 1–3 ml, and delivery by the subcutaneous route is preferred.

TABLE 1

TOTAL CLINICAL SCORES FOLLOWING CHALLENGE WITH FIPV

| CAT ID | Fever | Weight Loss | Leukopenia | Anemia | Chemical Signs | Death* | Total Score |
|---|---|---|---|---|---|---|---|
| SUBCUTANEOUS VACCINATES | | | | | | | |
| 1260 | 0 | 0 | 0 | 0 | 0 | 0 | 0 |
| 1262 | 1 | 0 | 0 | 0 | 0 | 0 | 1 |
| 1264 | 1 | 0 | 0 | 0 | 0 | 0 | 4 |
| 1266 | 0 | 0 | 0 | 0 | 0 | 0 | 0 |
| 1268 | 2 | 0 | 0 | 0 | 0 | 0 | 2 |
| INTRAMUSCULAR VACCINATES | | | | | | | |
| 1270 | 13 | 6 | 0 | 0 | 33 | 25 | 77 |
| 1272 | 2 | 0 | 0 | 0 | 0 | 0 | 2 |
| 1287 | 23 | 0 | 0 | 0 | 34 | 25 | 91 |
| 1299 | 3 | 0 | 0 | 0 | 1 | 0 | 4 |
| 1301 | 3 | 0 | 0 | 0 | 0 | 0 | 3 |
| ORAL VACCINATES | | | | | | | |
| 1303 | 1 | 0 | 4 | 0 | 0 | 0 | 5 |
| 1306 | 0 | 1 | 0 | 0 | 5 | 0 | 6 |
| 1307 | 3 | 1 | 0 | 0 | 4 | 25 | 33 |
| 1309 | 2 | 1 | 6 | 0 | 6 | 25 | 40 |
| 1311 | 4 | 3 | 0 | 0 | 18 | 25 | 50 |
| 1/10 DOSE SUBCUTANEOUS VACCINATES | | | | | | | |
| 1313 | 29 | 5 | 9 | 3 | 36 | 25 | 107 |
| 1316 | 17 | 0 | 0 | 0 | 20 | 25 | 62 |
| 1317 | 3 | 0 | 3 | 0 | 9 | 25 | 40 |
| 1319 | 1 | 0 | 0 | 0 | 6 | 0 | 7 |
| CONTROLS | | | | | | | |
| 1321 | 39 | 3 | 18 | 3 | 63 | 25 | 151 |
| 1323 | 5 | 0 | 2 | 0 | 14 | 25 | 46 |
| 1327 | 0 | 1 | 2 | 0 | 15 | 25 | 43 |
| 1329 | 5 | 1 | 6 | 0 | 11 | 25 | 48 |
| 1337 | 1 | 0 | 0 | 0 | 0 | 0 | 1 |

What is claimed is:

1. A recombinant raccoon poxvirus having at least one internal gene comprising a DNA sequence encoding the transmembrane (M/E1) protein of Feline Infectious Peritonitis Virus (FIPV).

2. The recombinant raccoon poxvirus of claim 1 wherein said internal gene encodes a polypeptide having the amino acid sequence of FIG. 1A, SEQ ID NO:5.

3. The recombinant raccoon poxvirus of claim 1 wherein said virus has genes encoding the E1 and N proteins of FIPV.

4. A vaccine comprising:

a recombinant raccoon poxvirus having at least one internal gene comprising a DNA sequence encoding the transmembrane (M/E1) protein of Feline Infectious Peritonitis Virus (FIPV), and a pharmaceutically acceptable carrier.

5. The vaccine of claim 4 wherein said internal gene encodes a polypeptide having the amino acid sequence as set out in FIG. 1A, SEQ ID NO:5.

6. The vaccine of claim 4 wherein said virus has genes encoding the E1 and N proteins of FIPV.

7. The vaccine of claim 4 further comprising inactivated or attenuated viruses selected from the group consisting of feline leukemia virus, feline panleucopenia virus, feline rhinotracheitis virus, feline calicivirus, feline immunodeficiency virus, feline herpesvirus, feline enteric coronavirus, and mixtures thereof.

8. The vaccine of claim 4 further comprising organisms selected from the group consisting of inactivated or attenuated feline *Chlamydia psittaci, Microsporum canis,* and mixtures thereof.

9. The vaccine of claim 4, further comprising a pharmaceutically acceptable adjuvant.

10. A vaccine comprising:

a first recombinant raccoon poxvirus having at least one internal gene comprising a DNA sequence encoding the transmembrane (M/E1) protein of Feline Infectious Peritonitis Virus (FIPV), a second recombinant raccoon poxvirus having at least one internal gene comprising a DNA sequence encoding the nucleocapsid (N) protein of Feline Infectious Peritonitis Virus (FIPV), a pharmaceutically acceptable carrier or diluent, and a pharmaceutically acceptable adjuvant.

11. A method for preventing disease caused by Feline Infectious Peritonitis Virus (FIPV), comprising administering to a feline in need of such treatment a vaccine comprising a recombinant raccoon poxvirus having at least one internal gene comprising a DNA sequence encoding the transmembrane (M/E1) protein of FIPV.

12. The method of claim 11 wherein said internal gene encodes a polypeptide having the amino acid sequence of FIG. 1A, SEQ ID NO:5.

13. The method of claim 11 wherein said virus has genes encoding the E1 and N proteins of FIPV.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
(A) LENGTH: 789 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Feline infectious peritonitis virus (vii) IMMEDIATE SOURCE:
(B) CLONE: FIPV E1

(xi) SEQUENCE DESCRIPTION: SEQ ID NO:1:

```
ATGAAGTACA TTTTGCTAAT ACTCGCGTGC ATAATTGCAT GCGTTTATGG TGAACGCTAC    60
TGTGCCATGC AAGACAGTGG CTTGCAGTGT ATTAATGGCA CAAATTCAAG ATGTCAAACC   120
TGCTTTGAAC GTGGTGATCT TATTTGGCAT CTTGCTAACT GGAACTTCAG CTGGTCTGTA   180
ATATTGATTG TTTTTATAAC AGTGTTACAA TATGGCAGAC CACAATTTAG CTGGCTCGTT   240
TATGGCATTA AAATGCTGAT CATGTGGCTA TTATGGCCTA TTGTTCTAGC GCTTACGATT   300
TTTAATGCAT ACTCTGAGTA CCAAGTTTCC AGATATGTAA TGTTCGGCTT TAGTGTTGCA   360
GGTGCAGTTG TAACGTTTGC ACTTTGGATG ATGTATTTTG TGAGATCTGT TCAGCTATAT   420
AGAAGAACCA AATCATGGTG GTCTTTTAAT CCTGAGACTA ATGCAATTCT TTGTGTTAAT   480
GCATTGGGTA GAAGTTATGT GCTTCCCTTA GATGGTACTC CTACAGGTGT TACCCTTACT   540
CTACTTTCAG GAAATCTATA TGCTGAAGGT TTCAAAATGG CTGGTGGTTT AACCATCGAG   600
CATTTGCCTA AATACGTCAT GATTGCTACA CCTAGTAGAA CCATCGTTTA TACATTAGTT   660
GGAAAACAAT TAAAAGCAAC TACTGCCACA GGATGGGCTT ACTACGTAAA ATCTAAAGCT   720
GGTGATTACT CAACAGAAGC ACGTACTGAC AATTTGAGTG AACATGAAAA ATTATTACAT   780
ATGGTGTAA                                                           789
```

(2) INFORMATION FOR SEQ ID NO:2:

(i) SEQUENCE CHARACTERISTICS:
(A) LENGTH: 1134 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Feline infectious peritonitis virus (vii) IMMEDIATE SOURCE:
(B) CLONE: FIPV N (xi) SEQUENCE DESCRIPTION: SEQ ID NO:2:

```
ATGGCCACAC AGGGACAACG CGTCAACTGG GGAGATGAAC CTTCCAAAAG ACGTGGTCGT    60
TCTAACTCTC GTGGTCGGAA GAATAATGAT ATACCTTTGT CATTCTACAA CCCCATTACC   120
CTCGAACAAG GATCTAAATT TTGGAATTTA TGTCCGAGAG ACCTTGTTCC CAAAGGAATA   180
GGTAATAAGG ATCAACAAAT TGGTTATTGG AATAGACAGA TTCGTTATCG TATTGTAAAA   240
```

-continued

```
GGCCAGCGTA AGGAACTCGC TGAGAGGTGG TTCTTTTACT TCTTAGGTAC AGGACCTCAT    300
GCTGATGCTA AATTCAAAGA CAAGATTGAT GGAGTCTTCT GGGTTGCAAG GGATGGTGCC    360
ATGAACAAGC CCACAACGCT TGGCACTCGT GGAACCAATA ACGAATCCAA ACCACTGAGA    420
TTTGATGGTA AGATACCGCC ACAGTTTCAG CTTGAAGTGA ACCGTTCTAG GAACAATTCA    480
AGGTCTGGTT CTCAGTCTAG ATCTGTTTCA AGAAACAGAT CTCAATCTAG AGGAAGACAC    540
CATTCCAATA ACCAGAATAA TAATGTTGAG GATACAATTG TAGCCGTGCT TGAAAAATTA    600
GGTGTTACTG ACAAACAAAG GTCACGTTCT AAACCTAGAG AACGTAGTGA TTCCAAACCT    660
AGGGACACAA CACCTAAGAA TGCCAACAAA CACACCTGGA AGAAAACTGC AGGCAAGGGA    720
GATGTGACAA CTTTCTATGG TGCTAGAAGT AGTTCAGCTA ACTTTGGTGA TAGTGATCTC    780
GTTGCCAATG GTAACGCTGC CAAATGCTAC CCTCAGATAG CTGAATGTGT TCCATCAGTG    840
TCTAGCATAA TCTTTGGCAG TCAATGGTCT GCTGAAGAAG CTGGTGATCA AGTGAAAGTC    900
ACGCTCACTC ACACCTACTA CCTGCCAAAG GATGATGCCA AAACTAGTCA ATTCCTAGAA    960
CAGATTGACG CTTACAAGCG ACCTTCTGAA GTGGCTAAGG ATCAGAGGCA AAGAAGATCC   1020
CGTTCTAAGT CTGCTGATAA GAAGCCTGAG GAGTTGTCTG TAACTCTTGT GGAGGCATAC   1080
ACAGATGTGT TTGATGACAC ACAGGTTGAG ATGATTGATG AGGTTACGAA CTAA         1134
```

( 2 ) INFORMATION FOR SEQ ID NO:3:

( i ) SEQUENCE CHARACTERISTICS:
( A ) LENGTH: 8710 base pairs
( B ) TYPE: nucleic acid
( C ) STRANDEDNESS: double
( D ) TOPOLOGY: circular ( i i ) MOLECULE TYPE: DNA (genomic)

( v i ) ORIGINAL SOURCE:
( A ) ORGANISM: Feline infectious peritonitis virus ( v i i ) IMMEDIATE SOURCE:
( B ) CLONE: psc11f1

( x i ) SEQUENCE DESCRIPTION: SEQ ID NO:3:

```
CGAAAGGGCC TCGTGATACG CCTATTTTTA TAGGTTAATG TCATGATAAT AATGGTTTCT     60
TAGACGTCAG GTGGCACTTT TCGGGGAAAT GTGCGCGGAA CCCCTATTTG TTTATTTTTC    120
TAAATACATT CAAATATGTA TCCGCTCATG AGACAATAAC CCTGATAAAT GCTTCAATAA    180
TATTGAAAAA GGAAGAGTAT GAGTATTCAA CATTTCCGTG TCGCCCTTAT TCCCTTTTTT    240
GCGGCATTTT GCCTTCCTGT TTTTGCTCAC CCAGAAACGC TGGTGAAAGT AAAAGATGCT    300
GAAGATCAGT TGGGTGCACG AGTGGGTTAC ATCGAACTGG ATCTCAACAG CGGTAAGATC    360
CTTGAGAGTT TTCGCCCCGA AGAACGTTTT CCAATGATGA GCACTTTTAA AGTTCTGCTA    420
TGTGGCGCGG TATTATCCCG TATTGACGCC GGGCAAGAGC AACTCGGTCG CCGCATACAC    480
TATTCTCAGA ATGACTTGGT TGAGTACTCA CCAGTCACAG AAAAGCATCT TACGGATGGC    540
ATGACAGTAA GAGAATTATG CAGTGCTGCC ATAACCATGA GTGATAACAC TGCGGCCAAC    600
TTACTTCTGA CAACGATCGG AGGACCGAAG GAGCTAACCG CTTTTTTGCA CAACATGGGG    660
GATCATGTAA CTCGCCTTGA TCGTTGGGAA CCGGAGCTGA ATGAAGCCAT ACCAAACGAC    720
GAGCGTGACA CCACGATGCC TGTAGCAATG GCAACAACGT TGCGCAAACT ATTAACTGGC    780
GAACTACTTA CTCTAGCTTC CCGGCAACAA TTAATAGACT GGATGGAGGC GGATAAAGTT    840
GCAGGACCAC TTCTGCGCTC GGCCCTTCCG GCTGGCTGGT TTATTGCTGA TAAATCTGGA    900
```

-continued

```
GCCGGTGAGC GTGGGTCTCG CGGTATCATT GCAGCACTGG GGCCAGATGG TAAGCCCTCC  960
CGTATCGTAG TTATCTACAC GACGGGGAGT CAGGCAACTA TGGATGAACG AAATAGACAG 1020
ATCGCTGAGA TAGGTGCCTC ACTGATTAAG CATTGGTAAC TGTCAGACCA AGTTTACTCA 1080
TATATACTTT AGATTGATTT AAAACTTCAT TTTTAATTTA AAAGGATCTA GGTGAAGATC 1140
CTTTTTGATA ATCTCATGAC CAAAATCCCT TAACGTGAGT TTTCGTTCCA CTGAGCGTCA 1200
GACCCCGTAG AAAAGATCAA AGGATCTTCT TGAGATCCTT TTTTTCTGCG CGTAATCTGC 1260
TGCTTGCAAA CAAAAAAACC ACCGCTACCA GCGGTGGTTT GTTTGCCGGA TCAAGAGCTA 1320
CCAACTCTTT TTCCGAAGGT AACTGGCTTC AGCAGAGCGC AGATACCAAA TACTGTCCTT 1380
CTAGTGTAGC CGTAGTTAGG CCACCACTTC AAGAACTCTG TAGCACCGCC TACATACCTC 1440
GCTCTGCTAA TCCTGTTACC AGTGGCTGCT GCCAGTGGCG ATAAGTCGTG TCTTACCGGG 1500
TTGGACTCAA GACGATAGTT ACCGGATAAG GCGCAGCGGT CGGGCTGAAC GGGGGGTTCG 1560
TGCACACAGC CCAGCTTGGA GCGAACGACC TACACCGAAC TGAGATACCT ACAGCGTGAG 1620
CATTGAGAAA GCGCCACGCT TCCCGAAGGG AGAAAGGCGG ACAGGTATCC GGTAAGCGGC 1680
AGGGTCGGAA CAGGAGAGCG CACGAGGGAG CTTCCAGGGG GAAACGCCTG GTATCTTTAT 1740
AGTCCTGTCG GGTTTCGCCA CCTCTGACTT GAGCGTCGAT TTTTGTGATG CTCGTCAGGG 1800
GGGCGGAGCC TATGGAAAAA CGCCAGCAAC GCGGCCTTTT TACGGTTCCT GGCCTTTTGC 1860
TGGCCTTTTG CTCACATGTT CTTTCCTGCG TTATCCCCTG ATTCTGTGGA TAACCGTATT 1920
ACCGCCTTTG AGTGAGCTGA TACCGCTCGC CGCAGCCGAA CGACCGAGCG CAGCGAGTCA 1980
GTGAGCGAGG AAGCGGAAGA GCGCCCAATA CGCAAACCGC CTCTCCCCGC GCGTTGGCCG 2040
ATTCATTAAT GCAGCTGGCA CGACAGGTTT CCCGACTGGA AAGCGGGCAG TGAGCGCAAC 2100
GCAATTAATG TGAGTTAGCT CACTCATTAG GCACCCCAGG CTTTACACTT TATGCTTCCG 2160
GCTCGTATGT TGTGTGGAAT TGTGAGCGGA TAACAATTTC ACACAGGAAA CAGCTATGAC 2220
CATGATTACG CCAAGCTTTT GCGATCAATA AATGGATCAC AACCAGTATC TCTTAACGAT 2280
GTTCTTCGCA GATGATGATT CATTTTTTAA GTATTTGGCT AGTCAAGATG ATGAAATCTT 2340
CATTATCTGA TATATTGCAA ATCACTCAAT ATCTAGACTT TCTGTTATTA TTATTGATCC 2400
AATCAAAAAA TAAATTAGAA GCCGTGGGTC ATTGTTATGA ATCTCTTTCA GAGGAATACA 2460
GACAATTGAC AAAATTCACA GACTTTCAAG ATTTTAAAAA ACTGTTTAAC AAGGTCCCTA 2520
TTGTTACAGA TGGAAGGGTC AAACTTAATA AAGGATATTT GTTCGACTTT GTGATTAGTT 2580
TGATGCGATT CAAAAAAGAA TCCTCTCTAG CTACCACCGC AATAGATCCT GTTAGATACA 2640
TAGATCCTCG TCGCAATATC GCATTTTCTA ACGTGATGGA TATATTAAAG TCGAATAAAG 2700
TGAACAATAA TTAATTCTTT ATTGTCATCA TGAACGGCGG ACATATTCAG TTGATAATCG 2760
GCCCCATGTT TTCAGGTAAA AGTACAGAAT TAATTAGACG AGTTAGACGT TATCAAATAG 2820
CTCAATATAA ATGCGTGACT ATAAAATATT CTAACGATAA TAGATACGGA ACGGGACTAT 2880
GGACGCATGA TAAGAATAAT TTTGAAGCAT TGGAAGCAAC TAAACTATGT GATCTCTTGG 2940
AATCAATTAC AGATTTCTCC GTGATAGGTA TCGATGAAGG ACAGTTCTTT CCAGACATTG 3000
TTGAATTCCG AGCTTGGCTG CAGGTCGGGG ATCCCCCCTG CCCGGTTATT ATTATTTTTG 3060
ACACCAGACC AACTGGTAAT GGTAGCGAAC GGCGCTCAGC TGAATTCCGC CGATACTGAC 3120
GGGCTCCAGG AGTCGTCGCC ACCAATCCCC ATATGGAAAC CGTCGATATT CAGCCATGTG 3180
CCTTCTTCCG CGTGCAGCAG ATGGCGATGG CTGGTTTCCA TCAGTTGCTG TTGACTGTAG 3240
CGGCTGATGT TGAACTGGAA GTCGCCGCGC CACTGGTGTG GGCCATAATT CAATTCGCGC 3300
```

-continued

| | | | | | | |
|---|---|---|---|---|---|---|
| GTCCCGCAGC | GCAGACCGTT | TTCGCTCGGG | AAGACGTACG | GGGTATACAT | GTCTGACAAT | 3360 |
| GGCAGATCCC | AGCGGTCAAA | ACAGGCGGCA | GTAAGGCGGT | CGGGATAGTT | TTCTTGCGGC | 3420 |
| CCTAATCCGA | GCCAGTTTAC | CCGCTCTGCT | ACCTGCGCCA | GCTGGCAGTT | CAGGCCAATC | 3480 |
| CGCGCCGGAT | GCGGTGTATC | GCTCGCCACT | TCAACATCAA | CGGTAATCGC | CATTTGACCA | 3540 |
| CTACCATCAA | TCCGGTAGGT | TTTCCGGCTG | ATAAATAAGG | TTTTCCCCTG | ATGCTGCCAC | 3600 |
| GCGTGACCGG | TCGTAATCAG | CACCGCATCA | GCAAGTGTAT | CTGCCGTGCA | CTGCAACAAC | 3660 |
| GCTGCTTCGG | CCTGGTAATG | GCCCGCCGCC | TTCCAGCGTT | CGACCCAGGC | GTTAGGGTCA | 3720 |
| ATGCGGGTCG | CTTCACTTAC | GCCAATGTCG | TTATCCAGCG | GTGCACGGGT | GAACTGATCG | 3780 |
| CGCAGCGGCG | TCAGCAGTTG | TTTTTTATCG | CCAATCCACA | TCTGTGAAAG | AAAGCCTGAC | 3840 |
| TGGCGGTTAA | ATTGCCAACG | CTTATTACCC | AGCTCGATGC | AAAAATCCAT | TTCGCTGGTG | 3900 |
| GTCAGATGCG | GGATGGCGTG | GGACGCGGCG | GGGAGCGTCA | CACTGAGGTT | TTCCGCCAGA | 3960 |
| CGCCACTGCT | GCCAGGCGCT | GATGTGCCCG | GCTTCTGACC | ATGCGGTCGC | GTTCGGTTGC | 4020 |
| ACTACGCGTA | CTGTGAGCCA | GAGTTGCCCG | GCGCTCTCCG | GCTGCGGTAG | TTCAGGCAGT | 4080 |
| TCAATCAACT | GTTTACCTTG | TGGAGCGACA | TCCAGAGGCA | CTTCACCGCT | TGCCAGCGGC | 4140 |
| TTACCATCCA | GCGCCACCAT | CCAGTGCAGG | AGCTCGTTAT | CGCTATGACG | GAACAGGTAT | 4200 |
| TCGCTGGTCA | CTTCGATGGT | TTGCCCGGAT | AAACGGAACT | GGAAAAACTG | CTGCTGGTGT | 4260 |
| TTTGCTTCCG | TCAGCGCTGG | ATGCGGCGTG | CGGTCGGCAA | AGACCAGACC | GTTCATACAG | 4320 |
| AACTGGCGAT | CGTTCGGCGT | ATCGCCAAAA | TCACCGCCGT | AAGCCGACCA | CGGGTTGCCG | 4380 |
| TTTTCATCAT | ATTTAATCAG | CGACTGATCC | ACCCAGTCCC | AGACGAAGCC | GCCCTGTAAA | 4440 |
| CGGGGATACT | GACGAAACGC | CTGCCAGTAT | TTAGCGAAAC | CGCCAAGACT | GTTACCCATC | 4500 |
| GCGTGGGCGT | ATTCGCAAAG | GATCAGCGGG | CGCGTCTCTC | CAGGTAGCGA | AAGCCATTTT | 4560 |
| TTGATGGACC | ATTTCGGCAC | AGCCGGGAAG | GGCTGGTCTT | CATCCACGCG | CGCGTACATC | 4620 |
| GGGCAAATAA | TATCGGTGGC | CGTGGTGTCG | GCTCCGCCGC | CTTCATACTG | CACCGGGCGG | 4680 |
| GAAGGATCGA | CAGATTTGAT | CCAGCGATAC | AGCGCGTCGT | GATTAGCGCC | GTGGCCTGAT | 4740 |
| TCATTCCCCA | GCGACCAGAT | GATCACACTC | GGGTGATTAC | GATCGCGCTG | CACCATTCGC | 4800 |
| GTTACGCGTT | CGCTCATCGC | CGGTAGCCAG | CGCGGATCAT | CGGTCAGACG | ATTGATTGGC | 4860 |
| ACCATGCCGT | GGGTTTCAAT | ATTGGCTTCA | TCCACCACAT | ACAGGCCGTA | GCGGTCGCAC | 4920 |
| AGCGTGTACC | ACAGCGGATG | GTTCGGATAA | TGCGAACAGC | GCACGGCGTT | AAAGTTGTTC | 4980 |
| TGCTTCATCA | GCAGGATATC | CTGCACCATC | GTCTGCTCAT | CCATGACCTG | ACCATGCAGA | 5040 |
| GGATGATGCT | CGTGACGGTT | AACGCCTCGA | ATCAGCAACG | GCTTGCCGTT | CAGCAGCAGC | 5100 |
| AGACCATTTT | CAATCCGCAC | CTCGCGGAAA | CCGACATCGC | AGGCTTCTGC | TTCAATCAGC | 5160 |
| GTGCCGTCGG | CGGTGTGCAG | TTCAACCACC | GCACGATAGA | GATTCGGGAT | TTCGGCGCTC | 5220 |
| CACAGTTTCG | GGTTTTCGAC | CTTGAGACGT | AGTGTGACGC | GATCGGCATA | ACCACCACGC | 5280 |
| TCATCGATAA | TTTCACCGCC | GAAAGGCGCG | GTGCCGCTGG | CGACCTGCGT | TTCACCCTGC | 5340 |
| CATAAAGAAA | CTGTTACCCG | TAGGTAGTCA | CGCAACTCGC | CGCACATCTG | AACTTCAGCC | 5400 |
| TCCAGTACAG | CGCGGCTGAA | ATCATCATTA | AAGCGAGTGG | CAACATGGAA | ATCGCTGATT | 5460 |
| TGTGTAGTCG | GTTTATGCAG | CAACGAGACG | TCACGGAAAA | TGCCGCTCAT | CCGCCACATA | 5520 |
| TCCTGATCTT | CCAGATAACT | GCCGTCACTC | CAACGCAGCA | CCATCACCGC | GAGGCGGTTT | 5580 |
| TCTCCGGCGC | GTAAAAATGC | GCTCAGGTCA | AATTCAGACG | GCAAACGACT | GTCCTGGCCG | 5640 |
| TAACCGACCC | AGCGCCCGTT | GCACCACAGA | TGAAACGCCG | AGTTAACGCC | ATCAAAAATA | 5700 |

-continued

ATTCGCGTCT GGCCTTCCTG TAGCCAGCTT TCATCAACAT TAAATGTGAG CGAGTAACAA 5760
CCCGTCGGAT TCTCCGTGGG AACAAACGGC GGATTGACCG TAATGGGATA GGTTACGTTG 5820
GTGTAGATGG GCGCATCGTA ACCGTGCATC TGCCAGTTTG AGGGGACGAC GACAGTATCG 5880
GCCTCAGGAA GATCGCACTC CAGCCAGCTT TCCGGCACCG CTTCTGGTGC CGGAAACCAG 5940
GCAAAGCGCC ATTCGCCATT CAGGCTGCGC AACTGTTGGG AAGGGCGATC GGTGCGGGCC 6000
TCTTCGCTAT TACGCCAGCT GGCGAAAGGG GGATGTGCTG CAAGGCGATT AAGTTGGGTA 6060
ACGCCAGGGT TTTCCCAGTC ACGACGTTGT AAAACGACGG GATCCCTCGA GGAATTCATT 6120
TATAGCATAG AAAAAAACAA AATGAAATTC TACTATATTT TTACATACAT ATATTCTAAA 6180
TATGAAAGTG GTGATTGTGA CTAGCGTAGC ATCGCTTCTA GACATATACT ATATAGTAAT 6240
ACCAATACTC AAGACTACGA AACTGATACA ATCTCTTATC ATGTGGGTAA TGTTCTCGAT 6300
GTCGAATAGC CATATGCCGG TAGTTGCGAT ATACATAAAC TGATCACTAA TTCCAAACCC 6360
ACCCGCTTTT TATAGTAAGT TTTTCACCCA TAAATAATAA ATACAATAAT TAATTTCTCG 6420
TAAAAGTAGA AAATATATTC TAATTTATTG CACGGTAAGG AAGTAGAATC ATAAAGAACA 6480
GTGACGGATC CCAATTCGGG CATTTTTGGT TTGAACTAAA CAAAATGAAG TACATTTTGC 6540
TAATACTCGC GTGCATAATT GCATGCGTTT ATGGTGAACG CTACTGTGCC ATGCAAGACA 6600
GTGGCTTGCA GTGTATTAAT GGCACAAATT CAAGATGTCA AACCTGCTTT GAACGTGGTG 6660
ATCTTATTTG GCATCTTGCT AACTGGAACT TCAGCTGGTC TGTAATATTG ATTGTTTTTA 6720
TAACAGTGTT ACAATATGGC AGACCACAAT TTAGCTGGCT CGTTTATGGC ATTAAAATGC 6780
TGATCATGTG GCTATTATGG CCTATTGTTC TAGCGCTTAC GATTTTTAAT GCATACTCTG 6840
AGTACCAAGT TTCCAGATAT GTAATGTTCG GCTTTAGTGT TGCAGGTGCA GTTGTAACGT 6900
TTGCACTTTG GATGATGTAT TTTGTGAGAT CTGTTCAGCT ATATAGAAGA ACCAAATCAT 6960
GGTGGTCTTT TAATCCTGAG ACTAATGCAA TTCTTTGTGT TAATGCATTG GGTAGAAGTT 7020
ATGTGCTTCC CTTAGATGGT ACTCCTACAG GTGTTACCCT TACTCTACTT TCAGGAAATC 7080
TATATGCTGA AGGTTTCAAA ATGGCTGGTG GTTTAACCAT CGAGCATTTG CCTAAATACG 7140
TCATGATTGC TACACCTAGT AGAACCATCG TTTATACATT AGTTGGAAAA CAATTAAAAG 7200
CAACTACTGC CACAGGATGG GCTTACTACG TAAAATCTAA AGCTGGTGAT TACTCAACAG 7260
AAGCACGTAC TGACAATTTG AGTGAACATG AAAAATTATT ACATATGGTG TAACTAAACT 7320
TTCAAATGGG GGAATTCTGT GAGCGTATGG CAAACGAAGG AAAAATTAGT TATAGTAGCC 7380
GCACTCGATG GGACATTTCA ACGTAAACCG TTTAATAATA TTTTGAATCT TATTCCATTA 7440
TCTGAAATGG TGGTAAAACT AACTGCTGTG TGTATGAAAT GCTTTAAGGA GGCTTCCTTT 7500
TCTAAACGAT TGGGTGAGGA AACCGAGATA GAAATAATAG GAGGTAATGA TATGTATCAA 7560
TCGGTGTGTA GAAAGTGTTA CATCGACTCA TAATATTATA TTTTTTATCT AAAAAACTAA 7620
AAATAAACAT TGATTAAATT TTAATATAAT ACTTAAAAAT GGATGTTGTG TCGTTAGATA 7680
AACCGTTTAT GTATTTTGAG GAAATTGATA ATGAGTTAGA TTACGAACCA GAAAGTGCAA 7740
ATGAGGTCGC AAAAAAACTG CCGTATCAAG GACAGTTAAA ACTATTACTA GGAGAATTAT 7800
TTTTTCTTAG TAAGTTACAG CGACACGGTA TATTAGATGG TGCCACCGTA GTGTATATAG 7860
GATCTGCTCC CGGTACACAT ATACGTTATT TGAGAGATCA TTTCTATAAT TTAGGAGTGA 7920
TCATCAAATG GATGCTAATT GACGGCCGCC ATCATGATCC TATTTTAAAT GGATTGCGTG 7980
ATGTGACTCT AGTGACTCGG TTCGTTGATG AGGAATATCT ACGATCCATC AAAAAACAAC 8040
TGCATCCTTC TAAGATTATT TTAATTTCTG ATGTGAGATC CAAACGAGGA GGAAATGAAC 8100

-continued

CTAGTACGGC GGATTTACTA AGTAATTACG CTCTACAAAA TGTCATGATT AGTATTTTAA 8160
ACCCCGTGGC GTCTAGTCTT AAATGGAGAT GCCCGTTTCC AGATCAATGG ATCAAGGACT 8220
TTTATATCCC ACACGGTAAT AAAATGTTAC AACCTTTTGC TCCTTCATAT TCAGGGCCGT 8280
CGTTTTACAA CGTCGTGACT GGGAAAACCC TGGCGTTACC CAACTTAATC GCCTTGCAGC 8340
ACATCCCCCT TTCGCCAGCT GGCGTAATAG CGAAGAGGCC CGCACCGATC GCCCTTCCCA 8400
ACAGTTGCGC AGCCTGAATG GCGAATGGCG CCTGATGCGG TATTTTCTCT TTACGCATCT 8460
GTGCGGTATT TCACACCGCA TATGGTGCAC TCTCAGTACC ATCTGCTCTG ATGCCGCATA 8520
GTTAAGCCAG TACACTCCGC TATCGCTACG TGACTGGGTC ATGGCTGCGC CCCGACACCC 8580
GCCAACACCC GCTGACGCGC CCTGACGGGC TTGTCTGCTC CCGGCATCCG CTTACAGACA 8640
AGCTGTGACC GTCTCCGGGA GCTGCATGTG TCAGAGGTTT TCACCGTCAT CACCGAAACG 8700
CGCGAGGCAG 8710

( 2 ) INFORMATION FOR SEQ ID NO:4:

( i ) SEQUENCE CHARACTERISTICS:
( A ) LENGTH: 9019 base pairs
( B ) TYPE: nucleic acid
( C ) STRANDEDNESS: double
( D ) TOPOLOGY: circular ( i i ) MOLECULE TYPE: DNA (genomic)

( v i ) ORIGINAL SOURCE:
( A ) ORGANISM: Feline immunodeficiency virus ( v i i ) IMMEDIATE SOURCE:
( B ) CLONE: psc11e1

( x i ) SEQUENCE DESCRIPTION: SEQ ID NO:4:

GAAAGGGCCT CGTGATACGC CTATTTTTAT AGGTTAATGT CATGATAATA ATGGTTTCTT 60
AGACGTCAGG TGGCACTTTT CGGGGAAATG TGCGCGGAAC CCCTATTTGT TTATTTTTCT 120
AAATACATTC AAATATGTAT CCGCTCATGA GACAATAACC CTGATAAATG CTTCAATAAT 180
ATTGAAAAAG GAAGAGTATG AGTATTCAAC ATTTCCGTGT CGCCCTTATT CCCTTTTTTG 240
CGGCATTTTG CCTTCCTGTT TTTGCTCACC CAGAAACGCT GGTGAAAGTA AAAGATGCTG 300
AAGATCAGTT GGGTGCACGA GTGGGTTACA TCGAACTGGA TCTCAACAGC GGTAAGATCC 360
TTGAGAGTTT TCGCCCCGAA GAACGTTTTC CAATGATGAG CACTTTTAAA GTTCTGCTAT 420
GTGGCGCGGT ATTATCCCGT ATTGACGCCG GGCAAGAGCA ACTCGGTCGC CGCATACACT 480
ATTCTCAGAA TGACTTGGTT GAGTACTCAC CAGTCACAGA AAAGCATCTT ACGGATGGCA 540
TGACAGTAAG AGAATTATGC AGTGCTGCCA TAACCATGAG TGATAACACT GCGGCCAACT 600
TACTTCTGAC AACGATCGGA GGACCGAAGG AGCTAACCGC TTTTTTGCAC AACATGGGGG 660
ATCATGTAAC TCGCCTTGAT CGTTGGGAAC CGGAGCTGAA TGAAGCCATA CCAAACGACG 720
AGCGTGACAC CACGATGCCT GTAGCAATGG CAACAACGTT GCGCAAACTA TTAACTGGCG 780
AACTACTTAC TCTAGCTTCC CGGCAACAAT TAATAGACTG GATGGAGGCG GATAAAGTTG 840
CAGGACCACT TCTGCGCTCG GCCCTTCCGG CTGGCTGGTT TATTGCTGAT AAATCTGGAG 900
CCGGTGAGCG TGGGTCTCGC GGTATCATTG CAGCACTGGG GCCAGATGGT AAGCCCTCCC 960
GTATCGTAGT TATCTACACG ACGGGGAGTC AGGCAACTAT GGATGAACGA AATAGACAGA 1020
TCGCTGAGAT AGGTGCCTCA CTGATTAAGC ATTGGTAACT GTCAGACCAA GTTTACTCAT 1080
ATATACTTTA GATTGATTTA AAACTTCATT TTTAATTTAA AAGGATCTAG GTGAAGATCC 1140
TTTTTGATAA TCTCATGACC AAAATCCCTT AACGTGAGTT TTCGTTCCAC TGAGCGTCAG 1200

-continued

```
ACCCCGTAGA AAAGATCAAA GGATCTTCTT GAGATCCTTT TTTTCTGCGC GTAATCTGCT 1260
GCTTGCAAAC AAAAAAACCA CCGCTACCAG CGGTGGTTTG TTTGCCGGAT CAAGAGCTAC 1320
CAACTCTTTT TCCGAAGGTA ACTGGCTTCA GCAGAGCGCA GATACCAAAT ACTGTCCTTC 1380
TAGTGTAGCC GTAGTTAGGC CACCACTTCA AGAACTCTGT AGCACCGCCT ACATACCTCG 1440
CTCTGCTAAT CCTGTTACCA GTGGCTGCTG CCAGTGGCGA TAAGTCGTGT CTTACCGGGT 1500
TGGACTCAAG ACGATAGTTA CCGGATAAGG CGCAGCGGTC GGGCTGAACG GGGGGTTCGT 1560
GCACACAGCC CAGCTTGGAG CGAACGACCT ACACCGAACT GAGATACCTA CAGCGTGAGC 1620
ATTGAGAAAG CGCCACGCTT CCCGAAGGGA GAAAGGCGGA CAGGTATCCG GTAAGCGGCA 1680
GGGTCGGAAC AGGAGAGCGC ACGAGGGAGC TTCCAGGGGG AAACGCCTGG TATCTTTATA 1740
GTCCTGTCGG GTTTCGCCAC CTCTGACTTG AGCGTCGATT TTTGTGATGC TCGTCAGGGG 1800
GGCGGAGCCT ATGGAAAAAC GCCAGCAACG CGGCCTTTTT ACGGTTCCTG GCCTTTTGCT 1860
GGCCTTTTGC TCACATGTTC TTTCCTGCGT TATCCCCTGA TTCTGTGGAT AACCGTATTA 1920
CCGCCTTTGA GTGAGCTGAT ACCGCTCGCC GCAGCCGAAC GACCGAGCGC AGCGAGTCAG 1980
TGAGCGAGGA AGCGGAAGAG CGCCCAATAC GCAAACCGCC TCTCCCCGCG CGTTGGCCGA 2040
TTCATTAATG CAGCTGGCAC GACAGGTTTC CCGACTGGAA AGCGGGCAGT GAGCGCAACG 2100
CAATTAATGT GAGTTAGCTC ACTCATTAGG CACCCCAGGC TTTACACTTT ATGCTTCCGG 2160
CTCGTATGTT GTGTGGAATT GTGAGCGGAT AACAATTTCA CACAGGAAAC AGCTATGACC 2220
ATGATTACGC CAAGCTTTTG CGATCAATAA ATGGATCACA ACCAGTATCT CTTAACGATG 2280
TTCTTCGCAG ATGATGATTC ATTTTTTAAG TATTTGGCTA GTCAAGATGA TGAAATCTTC 2340
ATTATCTGAT ATATTGCAAA TCACTCAATA TCTAGACTTT CTGTTATTAT TATTGATCCA 2400
ATCAAAAAAT AAATTAGAAG CCGTGGGTCA TTGTTATGAA TCTCTTTCAG AGGAATACAG 2460
ACAATTGACA AAATTCACAG ACTTTCAAGA TTTTAAAAAA CTGTTTAACA AGGTCCCTAT 2520
TGTTACAGAT GGAAGGGTCA AACTTAATAA AGGATATTTG TTCGACTTTG TGATTAGTTT 2580
GATGCGATTC AAAAAAGAAT CCTCTCTAGC TACCACCGCA ATAGATCCTG TTAGATACAT 2640
AGATCCTCGT CGCAATATCG CATTTTCTAA CGTGATGGAT ATATTAAAGT CGAATAAAGT 2700
GAACAATAAT TAATTCTTTA TTGTCATCAT GAACGGCGGA CATATTCAGT TGATAATCGG 2760
CCCCATGTTT TCAGGTAAAA GTACAGAATT AATTAGACGA GTTAGACGTT ATCAAATAGC 2820
TCAATATAAA TGCGTGACTA TAAAATATTC TAACGATAAT AGATACGGAA CGGGACTATG 2880
GACGCATGAT AAGAATAATT TTGAAGCATT GGAAGCAACT AAACTATGTG ATCTCTTGGA 2940
ATCAATTACA GATTTCTCCG TGATAGGTAT CGATGAAGGA CAGTTCTTTC CAGACATTGT 3000
TGAATTCCGA GCTTGGCTGC AGGTCGGGGA TCCCCCCTGC CCGGTTATTA TTATTTTTGA 3060
CACCAGACCA ACTGGTAATG GTAGCGAACG GCGCTCAGCT GAATTCCGCC GATACTGACG 3120
GGCTCCAGGA GTCGTCGCCA CCAATCCCCA TATGGAAACC GTCGATATTC AGCCATGTGC 3180
CTTCTTCCGC GTGCAGCAGA TGGCGATGGC TGGTTTCCAT CAGTTGCTGT TGACTGTAGC 3240
GGCTGATGTT GAACTGGAAG TCGCCGCGCC ACTGGTGTGG GCCATAATTC AATTCGCGCG 3300
TCCCGCAGCG CAGACCGTTT TCGCTCGGGA AGACGTACGG GGTATACATG TCTGACAATG 3360
GCAGATCCCA GCGGTCAAAA CAGGCGGCAG TAAGGCGGTC GGGATAGTTT TCTTGCGGCC 3420
CTAATCCGAG CCAGTTTACC CGCTCTGCTA CCTGCGCCAG CTGGCAGTTC AGGCCAATCC 3480
GCGCCGGATG CGGTGTATCG CTCGCCACTT CAACATCAAC GGTAATCGCC ATTTGACCAC 3540
TACCATCAAT CCGGTAGGTT TTCCGGCTGA TAAATAAGGT TTTCCCCTGA TGCTGCCACG 3600
```

-continued

CGTGACCGGT CGTAATCAGC ACCGCATCAG CAAGTGTATC TGCCGTGCAC TGCAACAACG 3660
CTGCTTCGGC CTGGTAATGG CCCGCCGCCT TCCAGCGTTC GACCCAGGCG TTAGGGTCAA 3720
TGCGGGTCGC TTCACTTACG CCAATGTCGT TATCCAGCGG TGCACGGGTG AACTGATCGC 3780
GCAGCGGCGT CAGCAGTTGT TTTTTATCGC CAATCCACAT CTGTGAAAGA AAGCCTGACT 3840
GGCGGTTAAA TTGCCAACGC TTATTACCCA GCTCGATGCA AAAATCCATT TCGCTGGTGG 3900
TCAGATGCGG GATGGCGTGG GACGCGGCGG GGAGCGTCAC ACTGAGGTTT TCCGCCAGAC 3960
GCCACTGCTG CCAGGCGCTG ATGTGCCCGG CTTCTGACCA TGCGGTCGCG TTCGGTTGCA 4020
CTACGCGTAC TGTGAGCCAG AGTTGCCCGG CGCTCTCCGG CTGCGGTAGT TCAGGCAGTT 4080
CAATCAACTG TTTACCTTGT GGAGCGACAT CCAGAGGCAC TTCACCGCTT GCCAGCGGCT 4140
TACCATCCAG CGCCACCATC CAGTGCAGGA GCTCGTTATC GCTATGACGG AACAGGTATT 4200
CGCTGGTCAC TTCGATGGTT TGCCCGGATA AACGGAACTG GAAAAACTGC TGCTGGTGTT 4260
TTGCTTCCGT CAGCGCTGGA TGCGGCGTGC GGTCGGCAAA GACCAGACCG TTCATACAGA 4320
ACTGGCGATC GTTCGGCGTA TCGCCAAAAT CACCGCCGTA AGCCGACCAC GGGTTGCCGT 4380
TTTCATCATA TTTAATCAGC GACTGATCCA CCCAGTCCCA GACGAAGCCG CCCTGTAAAC 4440
GGGGATACTG ACGAAACGCC TGCCAGTATT TAGCGAAACC GCCAAGACTG TTACCCATCG 4500
CGTGGGCGTA TTCGCAAAGG ATCAGCGGGC GCGTCTCTCC AGGTAGCGAA AGCCATTTTT 4560
TGATGGACCA TTTCGGCACA GCCGGGAAGG GCTGGTCTTC ATCCACGCGC GCGTACATCG 4620
GGCAAATAAT ATCGGTGGCC GTGGTGTCGG CTCCGCCGCC TTCATACTGC ACCGGGCGGG 4680
AAGGATCGAC AGATTTGATC CAGCGATACA GCGCGTCGTG ATTAGCGCCG TGGCCTGATT 4740
CATTCCCCAG CGACCAGATG ATCACACTCG GGTGATTACG ATCGCGCTGC ACCATTCGCG 4800
TTACGCGTTC GCTCATCGCC GGTAGCCAGC GCGGATCATC GGTCAGACGA TTGATTGGCA 4860
CCATGCCGTG GGTTTCAATA TTGGCTTCAT CCACCACATA CAGGCCGTAG CGGTCGCACA 4920
GCGTGTACCA CAGCGGATGG TTCGGATAAT GCGAACAGCG CACGGCGTTA AAGTTGTTCT 4980
GCTTCATCAG CAGGATATCC TGCACCATCG TCTGCTCATC CATGACCTGA CCATGCAGAG 5040
GATGATGCTC GTGACGGTTA ACGCCTCGAA TCAGCAACGG CTTGCCGTTC AGCAGCAGCA 5100
GACCATTTTC AATCCGCACC TCGCGGAAAC CGACATCGCA GGCTTCTGCT TCAATCAGCG 5160
TGCCGTCGGC GGTGTGCAGT TCAACCACCG CACGATAGAG ATTCGGGATT TCGGCGCTCC 5220
ACAGTTTCGG GTTTTCGACC TTGAGACGTA GTGTGACGCG ATCGGCATAA CCACCACGCT 5280
CATCGATAAT TTCACCGCCG AAAGGCGCGG TGCCGCTGGC GACCTGCGTT TCACCCTGCC 5340
ATAAAGAAAC TGTTACCCGT AGGTAGTCAC GCAACTCGCC GCACATCTGA ACTTCAGCCT 5400
CCAGTACAGC GCGGCTGAAA TCATCATTAA AGCGAGTGGC AACATGGAAA TCGCTGATTT 5460
GTGTAGTCGG TTTATGCAGC AACGAGACGT CACGGAAAAT GCCGCTCATC CGCCACATAT 5520
CCTGATCTTC CAGATAACTG CCGTCACTCC AACGCAGCAC CATCACCGCG AGGCGGTTTT 5580
CTCCGGCGCG TAAAAATGCG CTCAGGTCAA ATTCAGACGG CAAACGACTG TCCTGGCCGT 5640
AACCGACCCA GCGCCCGTTG CACCACAGAT GAAACGCCGA GTTAACGCCA TCAAAAATAA 5700
TTCGCGTCTG GCCTTCCTGT AGCCAGCTTT CATCAACATT AAATGTGAGC GAGTAACAAC 5760
CCGTCGGATT CTCCGTGGGA ACAAACGGCG GATTGACCGT AATGGGATAG GTTACGTTGG 5820
TGTAGATGGG CGCATCGTAA CCGTGCATCT GCCAGTTTGA GGGGACGACG ACAGTATCGG 5880
CCTCAGGAAG ATCGCACTCC AGCCAGCTTT CCGGCACCGC TTCTGGTGCC GGAAACCAGG 5940
CAAAGCGCCA TTCGCCATTC AGGCTGCGCA ACTGTTGGGA AGGGCGATCG GTGCGGGCCT 6000

-continued

| | | | | | | |
|---|---|---|---|---|---|---|
| CTTCGCTATT | ACGCCAGCTG | GCGAAAGGGG | GATGTGCTGC | AAGGCGATTA | AGTTGGGTAA | 6060 |
| CGCCAGGGTT | TTCCCAGTCA | CGACGTTGTA | AAACGACGGG | ATCCCTCGAG | GAATTCATTT | 6120 |
| ATAGCATAGA | AAAAAACAAA | ATGAAATTCT | ACTATATTTT | TACATACATA | TATTCTAAAT | 6180 |
| ATGAAAGTGG | TGATTGTGAC | TAGCGTAGCA | TCGCTTCTAG | ACATATACTA | TATAGTAATA | 6240 |
| CCAATACTCA | AGACTACGAA | ACTGATACAA | TCTCTTATCA | TGTGGGTAAT | GTTCTCGATG | 6300 |
| TCGAATAGCC | ATATGCCGGT | AGTTGCGATA | TACATAAACT | GATCACTAAT | TCCAAACCCA | 6360 |
| CCCGCTTTTT | ATAGTAAGTT | TTTCACCCAT | AAATAATAAA | TACAATAATT | AATTTCTCGT | 6420 |
| AAAAGTAGAA | AATATATTCT | AATTTATTGC | ACGGTAAGGA | AGTAGAATCA | TAAAGAACAG | 6480 |
| TGACGGATCC | CGGGATGGCC | ACACAGGGAC | AACGCGTCAA | CTGGGGAGAT | GAACCTTCCA | 6540 |
| AAAGACGTGG | TCGTTCTAAC | TCTCGTGGTC | GGAAGAATAA | TGATATACCT | TTGTCATTCT | 6600 |
| ACAACCCCAT | TACCCTCGAA | CAAGGATCTA | AATTTTGGAA | TTTATGTCCG | AGAGACCTTG | 6660 |
| TTCCCAAAGG | AATAGGTAAT | AAGGATCAAC | AAATTGGTTA | TTGGAATAGA | CAGATTCGTT | 6720 |
| ATCGTATTGT | AAAAGGCCAG | CGTAAGGAAC | TCGCTGAGAG | GTGGTTCTTT | TACTTCTTAG | 6780 |
| GTACAGGACC | TCATGCTGAT | GCTAAATTCA | AAGACAAGAT | TGATGGAGTC | TTCTGGGTTG | 6840 |
| CAAGGGATGG | TGCCATGAAC | AAGCCCACAA | CGCTTGGCAC | TCGTGGAACC | AATAACGAAT | 6900 |
| CCAAACCACT | GAGATTTGAT | GGTAAGATAC | CGCCACAGTT | TCAGCTTGAA | GTGAACCGTT | 6960 |
| CTAGGAACAA | TTCAAGGTCT | GGTTCTCAGT | CTAGATCTGT | TTCAAGAAAC | AGATCTCAAT | 7020 |
| CTAGAGGAAG | ACACCATTCC | AATAACCAGA | ATAATAATGT | TGAGGATACA | ATTGTAGCCG | 7080 |
| TGCTTGAAAA | ATTAGGTGTT | ACTGACAAAC | AAAGGTCACG | TTCTAAACCT | AGAGAACGTA | 7140 |
| GTGATTCCAA | ACCTAGGGAC | ACAACACCTA | AGAATGCCAA | CAAACACACC | TGGAAGAAAA | 7200 |
| CTGCAGGCAA | GGGAGATGTG | ACAACTTTCT | ATGGTGCTAG | AAGTAGTTCA | GCTAACTTTG | 7260 |
| GTGATAGTGA | TCTCGTTGCC | AATGGTAACG | CTGCCAAATG | CTACCCTCAG | ATAGCTGAAT | 7320 |
| GTGTTCCATC | AGTGTCTAGC | ATAATCTTTG | GCAGTCAATG | GTCTGCTGAA | GAAGCTGGTG | 7380 |
| ATCAAGTGAA | AGTCACGCTC | ACTCACACCT | ACTACCTGCC | AAAGGATGAT | GCCAAAACTA | 7440 |
| GTCAATTCCT | AGAACAGATT | GACGCTTACA | AGCGACCTTC | TGAAGTGGCT | AAGGATCAGA | 7500 |
| GGCAAAGAAG | ATCCCGTTCT | AAGTCTGCTG | ATAAGAAGCC | TGAGGAGTTG | TCTGTAACTC | 7560 |
| TTGTGGAGGC | ATACACAGAT | GTGTTTGATG | ACACACAGGT | TGAGATGATT | GATGAGGTTA | 7620 |
| CGAACTAAAC | GCATGCCCGG | GAATTCTGTG | AGCGTATGGC | AAACGAAGGA | AAAATTAGTT | 7680 |
| ATAGTAGCCG | CACTCGATGG | GACATTTCAA | CGTAAACCGT | TTAATAATAT | TTTGAATCTT | 7740 |
| ATTCCATTAT | CTGAAATGGT | GGTAAAACTA | ACTGCTGTGT | GTATGAAATG | CTTTAAGGAG | 7800 |
| GCTTCCTTTT | CTAAACGATT | GGGTGAGGAA | ACCGAGATAG | AAATAATAGG | AGGTAATGAT | 7860 |
| ATGTATCAAT | CGGTGTGTAG | AAAGTGTTAC | ATCGACTCAT | AATATTATAT | TTTTTATCTA | 7920 |
| AAAAACTAAA | AATAAACATT | GATTAAATTT | TAATATAATA | CTTAAAAATG | GATGTTGTGT | 7980 |
| CGTTAGATAA | ACCGTTTATG | TATTTTGAGG | AAATTGATAA | TGAGTTAGAT | TACGAACCAG | 8040 |
| AAAGTGCAAA | TGAGGTCGCA | AAAAAACTGC | CGTATCAAGG | ACAGTTAAAA | CTATTACTAG | 8100 |
| GAGAATTATT | TTTTCTTAGT | AAGTTACAGC | GACACGGTAT | ATTAGATGGT | GCCACCGTAG | 8160 |
| TGTATATAGG | ATCTGCTCCC | GGTACACATA | TACGTTATTT | GAGAGATCAT | TTCTATAATT | 8220 |
| TAGGAGTGAT | CATCAAATGG | ATGCTAATTG | ACGGCCGCCA | TCATGATCCT | ATTTTAAATG | 8280 |
| GATTGCGTGA | TGTGACTCTA | GTGACTCGGT | TCGTTGATGA | GGAATATCTA | CGATCCATCA | 8340 |
| AAAAACAACT | GCATCCTTCT | AAGATTATTT | TAATTTCTGA | TGTGAGATCC | AAACGAGGAG | 8400 |

-continued

```
GAAATGAACC TAGTACGGCG GATTTACTAA GTAATTACGC TCTACAAAAT GTCATGATTA   8460
GTATTTTAAA CCCCGTGGCG TCTAGTCTTA AATGGAGATG CCCGTTTCCA GATCAATGGA   8520
TCAAGGACTT TTATATCCCA CACGGTAATA AAATGTTACA ACCTTTTGCT CCTTCATATT   8580
CAGGGCCGTC GTTTTACAAC GTCGTGACTG GGAAAACCCT GGCGTTACCC AACTTAATCG   8640
CCTTGCAGCA CATCCCCCTT TCGCCAGCTG GCGTAATAGC GAAGAGGCCC GCACCGATCG   8700
CCCTTCCCAA CAGTTGCGCA GCCTGAATGG CGAATGGCGC CTGATGCGGT ATTTTCTCTT   8760
TACGCATCTG TGCGGTATTT CACACCGCAT ATGGTGCACT CTCAGTACCA TCTGCTCTGA   8820
TGCCGCATAG TTAAGCCAGT ACACTCCGCT ATCGCTACGT GACTGGGTCA TGGCTGCGCC   8880
CCGACACCCG CCAACACCCG CTGACGCGCC CTGACGGGCT TGTCTGCTCC CGGCATCCGC   8940
TTACAGACAA GCTGTGACCG TCTCCGGGAG CTGCATGTGT CAGAGGTTTT CACCGTCATC   9000
ACCGAAACGC GCGAGGCAG                                                9019
```

( 2 ) INFORMATION FOR SEQ ID NO:5:

( i ) SEQUENCE CHARACTERISTICS:
( A ) LENGTH: 262 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Feline infectious peritonitis virus ( v i i ) IMMEDIATE SOURCE:
( B ) CLONE: FIPV E1

( x i ) SEQUENCE DESCRIPTION: SEQ ID NO:5:

```
Met Lys Tyr Ile Leu Leu Ile Leu Ala Cys Ile Ile Ala Cys Val Tyr
 1               5                  10                  15

Gly Glu Arg Tyr Cys Ala Met Gln Asp Ser Gly Leu Gln Cys Ile Asn
            20                  25                  30

Gly Thr Asn Ser Arg Cys Gln Thr Cys Phe Glu Arg Gly Asp Leu Ile
        35                  40                  45

Trp His Leu Ala Asn Trp Asn Phe Ser Trp Ser Val Ile Leu Ile Val
    50                  55                  60

Phe Ile Thr Val Leu Gln Tyr Gly Arg Pro Gln Phe Ser Trp Leu Val
65                  70                  75                  80

Tyr Gly Ile Lys Met Leu Ile Met Trp Leu Leu Trp Pro Ile Val Leu
                85                  90                  95

Ala Leu Thr Ile Phe Asn Ala Tyr Ser Glu Tyr Gln Val Ser Arg Tyr
            100                 105                 110

Val Met Phe Gly Phe Ser Val Ala Gly Ala Val Val Thr Phe Ala Leu
        115                 120                 125

Trp Met Met Tyr Phe Val Arg Ser Val Gln Leu Tyr Arg Arg Thr Lys
    130                 135                 140

Ser Trp Trp Ser Phe Asn Pro Glu Thr Asn Ala Ile Leu Cys Val Asn
145                 150                 155                 160

Ala Leu Gly Arg Ser Tyr Val Leu Pro Leu Asp Gly Thr Pro Thr Gly
                165                 170                 175
```

-continued

Val Thr Leu Thr Leu Leu Ser Gly Asn Leu Tyr Ala Glu Gly Phe Lys
180 185 190

Met Ala Gly Gly Leu Thr Ile Glu His Leu Pro Lys Tyr Val Met Ile
195 200 205

Ala Thr Pro Ser Arg Thr Ile Val Tyr Thr Leu Val Gly Lys Gln Leu
210 215 220

Lys Ala Thr Thr Ala Thr Gly Trp Ala Tyr Tyr Val Lys Ser Lys Ala
225 230 235 240

Gly Asp Tyr Ser Thr Glu Ala Arg Thr Asp Asn Leu Ser Glu His Glu
245 250 255

Lys Leu Leu His Met Val
260

( 2 ) INFORMATION FOR SEQ ID NO:6:

( i ) SEQUENCE CHARACTERISTICS:
( A ) LENGTH: 377 amino acids
( B ) TYPE: amino acid
( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
( A ) ORGANISM: Feline infectious peritonitis virus ( v i i ) IMMEDIATE SOURCE:
( B ) CLONE: FIPV N ( x i ) SEQUENCE DESCRIPTION: SEQ ID NO:6:

Met Ala Thr Gln Gly Gln Arg Val Asn Trp Gly Asp Glu Pro Ser Lys
1 5 10 15

Arg Arg Gly Arg Ser Asn Ser Arg Gly Arg Lys Asn Asn Asp Ile Pro
20 25 30

Leu Ser Phe Tyr Asn Pro Ile Thr Leu Glu Gln Gly Ser Lys Phe Trp
35 40 45

Asn Leu Cys Pro Arg Asp Leu Val Pro Lys Gly Ile Gly Asn Lys Asp
50 55 60

Gln Gln Ile Gly Tyr Trp Asn Arg Gln Ile Arg Tyr Arg Ile Val Lys
65 70 75 80

Gly Gln Arg Lys Glu Leu Ala Glu Arg Trp Phe Phe Tyr Phe Leu Gly
85 90 95

Thr Gly Pro His Ala Asp Ala Lys Phe Lys Asp Lys Ile Asp Gly Val
100 105 110

Phe Trp Val Ala Arg Asp Gly Ala Met Asn Lys Pro Thr Thr Leu Gly
115 120 125

Thr Arg Gly Thr Asn Asn Glu Ser Lys Pro Leu Arg Phe Asp Gly Lys
130 135 140

Ile Pro Pro Gln Phe Gln Leu Glu Val Asn Arg Ser Arg Asn Asn Ser
145 150 155 160

Arg Ser Gly Ser Gln Ser Arg Ser Val Ser Arg Asn Arg Ser Gln Ser
165 170 175

Arg Gly Arg His His Ser Asn Asn Gln Asn Asn Asn Val Glu Asp Thr
180 185 190

-continued

| | | | | | | | | | | | | | | | |
|---|---|---|---|---|---|---|---|---|---|---|---|---|---|---|---|
| Ile | Val | Ala 195 | Val | Leu | Glu | Lys | Leu 200 | Gly | Val | Thr | Asp | Lys 205 | Gln | Arg | Ser |
| Arg | Ser 210 | Lys | Pro | Arg | Glu | Arg 215 | Ser | Asp | Ser | Lys | Pro 220 | Arg | Asp | Thr | Thr |
| Pro 225 | Lys | Asn | Ala | Asn | Lys 230 | His | Thr | Trp | Lys | Lys 235 | Thr | Ala | Gly | Lys | Gly 240 |
| Asp | Val | Thr | Thr | Phe 245 | Tyr | Gly | Ala | Arg | Ser 250 | Ser | Ser | Ala | Asn | Phe 255 | Gly |
| Asp | Ser | Asp | Leu 260 | Val | Ala | Asn | Gly | Asn 265 | Ala | Ala | Lys | Cys | Tyr 270 | Pro | Gln |
| Ile | Ala | Glu 275 | Cys | Val | Pro | Ser | Val 280 | Ser | Ser | Ile | Ile | Phe 285 | Gly | Ser | Gln |
| Trp | Ser 290 | Ala | Glu | Glu | Ala | Gly 295 | Asp | Gln | Val | Lys | Val 300 | Thr | Leu | Thr | His |
| Thr 305 | Tyr | Tyr | Leu | Pro | Lys 310 | Asp | Asp | Ala | Lys | Thr 315 | Ser | Gln | Phe | Leu | Glu 320 |
| Gln | Ile | Asp | Ala | Tyr 325 | Lys | Arg | Pro | Ser | Glu 330 | Val | Ala | Lys | Asp | Gln 335 | Arg |
| Gln | Arg | Arg | Ser 340 | Arg | Ser | Lys | Ser | Ala 345 | Asp | Lys | Lys | Pro | Glu 350 | Glu | Leu |
| Ser | Val | Thr 355 | Leu | Val | Glu | Ala | Tyr 360 | Thr | Asp | Val | Phe | Asp 365 | Asp | Thr | Gln |
| Val | Glu 370 | Met | Ile | Asp | Glu | Val 375 | Thr | Asn | | | | | | | |

( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: N primer #1

( x i ) SEQUENCE DESCRIPTION: SEQ ID NO:7:

CTCGTGGTCG GAAGAATAAT GATA 24

( 2 ) INFORMATION FOR SEQ ID NO:8:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: N primer #2

( x i ) SEQUENCE DESCRIPTION: SEQ ID NO:8:

AGCACCATAG AAAGTTGTCA CATC 24

( 2 ) INFORMATION FOR SEQ ID NO:9:

-continued ( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: E1 primer #1

( x i ) SEQUENCE DESCRIPTION: SEQ ID NO:9:

TATGTAATGT TCGGCTTTAG TG 22

( 2 ) INFORMATION FOR SEQ ID NO:10:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: Other nucleic acid ( v i ) ORIGINAL SOURCE:
( A ) ORGANISM: Feline infectious peritonitis virus ( v i i ) IMMEDIATE SOURCE:
( B ) CLONE: E1 primer #2

( x i ) SEQUENCE DESCRIPTION: SEQ ID NO:10:

GTGCTTCTGT TGAGTAATCA CC 22